US009433393B2

(12) United States Patent
Takemoto et al.

(10) Patent No.: US 9,433,393 B2
(45) Date of Patent: Sep. 6, 2016

(54) IMAGE PROCESSING APPARATUS AND X-RAY DIAGNOSIS APPARATUS

(71) Applicant: Toshiba Medical Systems Corporation, Otawara-shi (JP)

(72) Inventors: Hisato Takemoto, Amherst, MA (US); Takuya Sakaguchi, Utsunomiya (JP); Yiemeng Hoi, Mundelein, IL (US)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/541,753

(22) Filed: Nov. 14, 2014

(65) Prior Publication Data

US 2015/0071520 A1    Mar. 12, 2015

Related U.S. Application Data

(63) Continuation of application No. PCT/JP2013/065882, filed on Jun. 7, 2013.

(30) Foreign Application Priority Data

Jun. 7, 2012  (JP) ................................ 2012-129980
Jun. 7, 2013  (JP) ................................ 2013-121021

(51) Int. Cl.
*G06K 9/00*      (2006.01)
*A61B 6/00*      (2006.01)

(52) U.S. Cl.
CPC .............. *A61B 6/481* (2013.01); *A61B 6/486* (2013.01); *A61B 6/504* (2013.01); *A61B 6/5211* (2013.01); *A61B 6/5217* (2013.01); *A61B 6/5264* (2013.01)

(58) Field of Classification Search
None
See application file for complete search history.

(56) References Cited

U.S. PATENT DOCUMENTS 8,050,474 B2    11/2011   Baumgart
2006/0078182 A1*  4/2006   Zwirn .................. G06T 7/0012
                                                    382/128

(Continued)

FOREIGN PATENT DOCUMENTS

JP    2003-299646 A    10/2003
JP    2010-022667 A     2/2010

(Continued)

OTHER PUBLICATIONS

U.S. Appl. No. 14/533,622, filed Nov. 5, 2014, Nagae, et al.

(Continued)

*Primary Examiner* — Hadi Akhavannik
(74) *Attorney, Agent, or Firm* — Oblon, McClelland, Maier & Neustadt, L.L.P

(57) ABSTRACT

An X-ray diagnosis apparatus includes: a reference value calculating unit that calculates a reference value used for normalizing a flow of a contrast material, on the basis of a chronological transition of a signal intensity of the contrast material in a predetermined region, for each of a plurality of groups of X-ray images chronologically taken while using the contrast material; an index image generating unit that normalizes, for each of the plurality of groups of X-ray images, the flow of the contrast material at each of pixels by using the reference value calculated by the reference value calculating unit and that generates an image in which a feature value of the normalized flow of the contrast material is reflected in each of the pixels; and a displayed image calculating unit that causes a predetermined display unit to display the image generated by the index image generating unit.

19 Claims, 13 Drawing Sheets

(56) References Cited

U.S. PATENT DOCUMENTS

2009/0141854 A1* 6/2009 Hirokawa .............. A61B 6/032
378/4
2009/0274358 A1* 11/2009 Flohr .................... A61B 6/032
382/131

FOREIGN PATENT DOCUMENTS

| JP | 2010-240255 A | 10/2010 |
|----|---------------|---------|
| JP | 2011-160978 A | 8/2011 |
| JP | 2011-172819 A | 9/2011 |
| WO | WO 2010-119355 A1 | 10/2010 |
| WO | WO 2011-151752 A1 | 12/2011 |

OTHER PUBLICATIONS

International Search Report issued on Jul. 16, 2013 for PCT/JP2013/065882 filed on Jun. 7, 2013 with English Translation.

International Written Opinion mailed on Jul. 16, 2013 for PCT/JP2013/065882 filed on Jun. 7, 2013.

Vogel, R.A. "The Radiographic Assessment of Coronary Blood Flow Parameters." *Circulation Journal of the American Heart Association*, 1985, vol. 72, pp. 460-465, Dallas, Texas.

U.S. Appl. 14/672,875, filed Mar. 30, 2015, Sakaguchi, et al.

* cited by examiner

<PT IMAGE>

IMAGE PROCESSING APPARATUS AND X-RAY DIAGNOSIS APPARATUS

CROSS-REFERENCE TO RELATED APPLICATION(S)

This application is a continuation of PCT international application Ser. No. PCT/JP2013/065882 filed on Jun. 7, 2013 which designates the United States, incorporated herein by reference, and which claims the benefit of priority from Japanese Patent Application No. 2012-129980, filed on Jun. 7, 2012 and Japanese Patent Application No. 2013-121021, filed on Jun. 7, 2013, the entire contents of which are incorporated herein by reference.

FIELD

Embodiments described herein relate generally to an image processing apparatus and an X-ray diagnosis apparatus.

BACKGROUND

Conventionally, to allow users to view structures of blood vessels through angiography image taking processes, an X-ray diagnosis apparatus performs a Digital Subtraction Angiography (DSA) image taking process. The DSA image taking process implements an image taking method by which an X-ray image (hereinafter, a "mask image", as necessary) showing a state where no contrast material has been injected and an X-ray image (hereinafter, a "contrast image", as necessary) showing a state where a contrast material has been injected are taken so as to perform a subtraction process between these images and to acquire a DSA image in which only the blood vessels are rendered.

In this situation, the DSA image is generated by performing the subtraction process between the two types of images, namely, the mask image and the contrast image. Thus, if the subject of the images moves, a positional misalignment may occur, in some situations, between the two types of images in a background element such as a bone, for example. In that situation, a region having signal intensities of pseudo signals occurs, although the region does not actually represent a blood vessel of which the contrast is enhanced by the contrast material. Such a region is viewed as an artifact in the DSA image.

To cope with this problem, a technique is known by which a subtraction process is performed after a position alignment process is performed on a mask image and a contrast image. According to this conventional technique, however, there is a certain limit to the visibility of angiography images.

DETAILED DESCRIPTION

According to embodiment, an image processing apparatus comprising, a reference value calculating unit, a generating unit and a display controlling unit. The reference value calculating unit that calculates a reference value used for normalizing a flow of a contrast material, on a basis of a chronological transition of a signal intensity of the contrast material in a predetermined region, for each of a plurality of groups of X-ray images chronologically taken while using the contrast material. The generating unit that, for each of the plurality of groups of X-ray images, normalizes the flow of the contrast material at each of pixels by using the reference value calculated by the reference value calculating unit and generates an image in which a feature value of the normalized flow of the contrast material is reflected in each of the pixels. The display controlling unit that causes a predetermined display unit to display the image generated by the generating unit.

Exemplary embodiments of an image processing apparatus and an X-ray diagnosis apparatus disclosed herein will be explained in detail below, with reference to the accompanying drawings. In the following sections, an example in which the image processing apparatus disclosed herein is incorporated in the X-ray diagnosis apparatus will be explained as an exemplary embodiment. It should be noted, however, that the image processing apparatus and the X-ray diagnosis apparatus disclosed herein are not limited to the exemplary embodiments described below.

Figure 1:
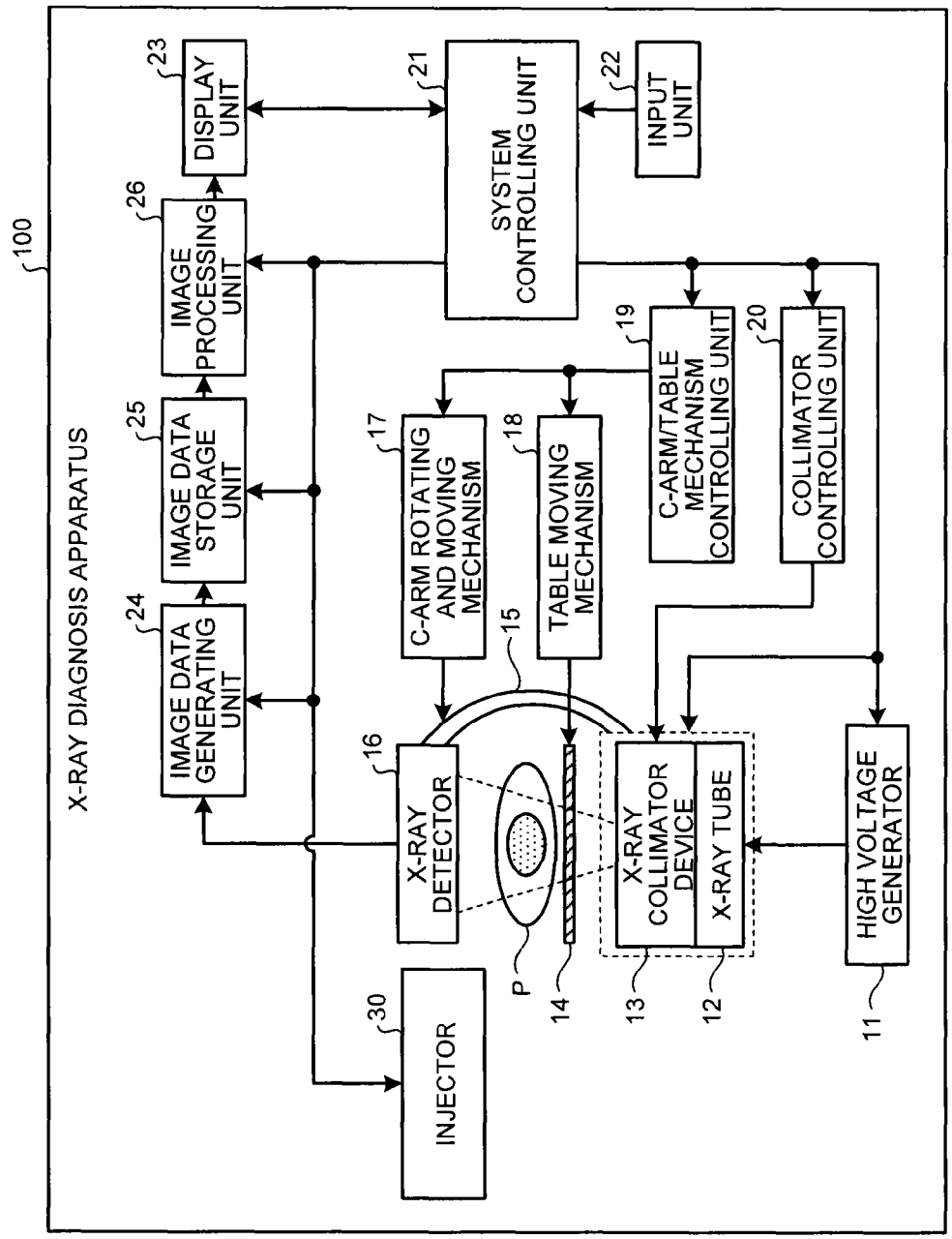
FIG. 1 is a diagram of an exemplary configuration of an X-ray diagnosis apparatus according to a first embodiment.

FIG. 1 is a diagram of an exemplary configuration of an X-ray diagnosis apparatus 100 according to a first embodiment. As shown in FIG. 1, the X-ray diagnosis apparatus 100 according to the first embodiment includes a high voltage generator 11, an X-ray tube 12, an X-ray collimator device 13, a table 14, a C-arm 15, and an X-ray detector 16. Further, the X-ray diagnosis apparatus 100 according to the first embodiment also includes a C-arm rotating and moving mechanism 17, a table moving mechanism 18, a C-arm/table mechanism controlling unit 19, a collimator controlling unit 20, a system controlling unit 21, an input unit 22, and a display unit 23. Further, the X-ray diagnosis apparatus 100 according to the first embodiment also includes an image data generating unit 24, an image data storage unit 25, and an image processing unit 26. Further, the X-ray diagnosis apparatus 100 is connected to an injector 30.

The injector 30 is a device used for injecting a contrast material through a catheter inserted into an examined subject P. In this situation, an injection of the contrast material from the injector 30 may be started according to an injection start instruction received via the system controlling unit 21 (explained later) or may be started according to an injection start instruction that is directly input to the injector 30 by an operator.

The high voltage generator 11 is configured to, under control of the system controlling unit 21, generate a high voltage and supply the generated high voltage to the X-ray tube 12. The X-ray tube 12 is configured to generate X-rays by using the high voltage supplied from the high voltage generator 11.

The X-ray collimator device 13 is configured to, under control of the collimator controlling unit 20, limit the beams of the X-rays generated by the X-ray tube 12 so as to be selectively radiated onto a region of interest of the subject P. For example, the X-ray collimator device 13 includes four collimator blades that are slidable. Under the control of the collimator controlling unit 20, by sliding the collimator blades, the X-ray collimator device 13 limits the beams of the X-rays generated by the X-ray tube 12 so as to be radiated onto the subject P. The table 14 is a bed on which the subject P is placed and is arranged over a couch (not shown). The subject P is not included in the X-ray diagnosis apparatus 100.

The X-ray detector 16 is configured to detect X-rays that have passed through the subject P. For example, the X-ray detector 16 includes detecting elements arranged in a matrix formation. The detecting elements are configured to convert the X-rays that have passed through the subject P into electric signals, to accumulate the electric signals therein, and to transmit the accumulated electric signals to the image data generating unit 24.

The C-arm 15 holds the X-ray tube 12, the X-ray collimator device 13, and the X-ray detector 16. The X-ray tube 12 and the X-ray collimator device 13 are arranged by the C-arm 15 so as to face the X-ray detector 16, while the subject P is interposed therebetween.

The C-arm rotating and moving mechanism 17 is a mechanism configured to rotate and move the C-arm 15, whereas the table moving mechanism 18 is a mechanism configured to move the table 14. The C-arm/table mechanism controlling unit 19 is configured to, under the control of the system controlling unit 21, regulate the rotation and the moving of the C-arm 15 as well as the moving of the table 14, by controlling the C-arm rotating and moving mechanism 17 and the table moving mechanism 18. The collimator controlling unit 20 is configured to, under the control of the system controlling unit 21, control the radiation range of the X-rays radiated onto the subject P, by adjusting the opening degrees of the collimator blades included in the X-ray collimator device 13.

The image data generating unit 24 is configured to generate image data by using the electric signals converted from the X-rays by the X-ray detector 16 and to store the generated image data into the image data storage unit 25. For example, the image data generating unit 24 generates the image data by applying a current/voltage conversion, an analog/digital (A/D) conversion, a parallel/serial conversion, and/or the like, on the electric signals received from the X-ray detector 16.

The image data storage unit 25 is configured to store therein the image data generated by the image data generating unit 24. For example, the image data storage unit 25 stores therein image data obtained by taking images, along a time series, of a predetermined region of the subject P into whom a contrast material has been injected. Further, the image data storage unit 25 is also configured to store therein a time-density image generated by the image processing unit 26. The time-density image will be explained in detail later.

The image processing unit 26 is configured to perform various types of image processing processes on the image data stored in the image data storage unit 25. The image processing processes performed by the image processing unit 26 will be explained in detail later.

The input unit 22 is configured to receive various types of instructions from the operator (e.g., a medical doctor, a technician, or the like) who operates the X-ray diagnosis apparatus 100. For example, the input unit 22 includes a mouse, a keyboard, a button, a trackball, a joystick, and/or the like. The input unit 22 is configured to transfer the instructions received from the operator to the system controlling unit 21.

The display unit 23 is configured to display a Graphical User Interface (GUI) used for receiving instructions from the operator and the image data stored in the image data storage unit 25. For example, the display unit 23 includes a monitor. The display unit 23 may include a plurality of monitors.

The system controlling unit 21 is configured to control operations in the entirety of the X-ray diagnosis apparatus 100. For example, the system controlling unit 21 controls the high voltage generator 11 according to an operator's instruction transferred from the input unit 22, so as to control the amount of X-rays radiated onto the subject P and to control on/off state, by adjusting the voltage supplied to the X-ray tube 12. Further, for example, the system controlling unit 21 controls the C-arm/table mechanism controlling unit 19 according to an operator's instruction, so as to regulate the rotation and the moving of the C-arm 15 and the moving of the table 14. Further, for example, the system controlling unit 21 controls the collimator controlling unit 20 according to an operator's instruction so as to control the radiation range of the X-rays radiated onto the subject P, by adjusting the opening degree of the collimator blades included in the X-ray collimator device 13.

Further, according to an operator's instruction, the system controlling unit 21 controls the image data generating process performed by the image data generating unit 24, the image processing processes or analyzing processes performed by the image processing unit 26. Further, the system controlling unit 21 exercises control so that the GUI used for receiving the operator's instructions and the images stored in the image data storage unit 25 are displayed on the monitor of the display unit 23. Further, the system controlling unit 21 controls timing with which the contrast material is injected, by transmitting signals to the injector 30 to indicate a start and an end of the injection of the contrast material.

The X-ray diagnosis apparatus 100 according to the first embodiment makes it possible to improve visibility of angiography images. More specifically, the X-ray diagnosis apparatus 100 improves visibility of the angiography images by expressing a flow of the contrast material in the angiography images in color images, as a result of the processes performed by the image processing unit 26 which are explained in detail below.

For example, when a thrombus removal method employing a catheter is implemented on a subject who had cerebral infarction, first, an angiography image is taken prior to a treatment, so as to make a diagnosis regarding a blood-vessel occluded region (an affected site). Subsequently, when a diagnosis regarding the position and the state of the affected site is made, a catheter is inserted into the affected site, so as to remove a thrombus. After that, an angiography image is taken again so as to judge whether the occlusion portion in the blood vessel is properly reopened or not. In this manner, during an intervascular treatment such as the one implementing the thrombus removal method on a subject who had cerebral infarction while employing a catheter, angiography images are taken before and after the treatment. After that, a medical doctor compares the images taken before and after the treatment with each other so as to observe signal intensities, the speed of the blood flow, and the like, in a comprehensive and intuitive manner.

In this situation, DSA images have conventionally been used as the angiography images. The DSA images are difference images obtained by performing a subtraction process between a mask image taken in the state where no contrast material has been injected and a contrast image taken in the state where the contrast material has been injected, so as to remove background elements such as bones. At present, for observations of blood vessels using such DSA images, monochrome DSA images are mainly used, and it is sometimes difficult to intuitively understand the state of the blood flow. Thus, there is a certain limit to the level of visibility.

To cope with this situation, the X-ray diagnosis apparatus 100 disclosed herein is configured to improve the visibility of angiography images and to enhance the level of precision of diagnoses, by expressing, in color images, the flow of the contrast material reflecting the state of the blood flow.

Figure 2:
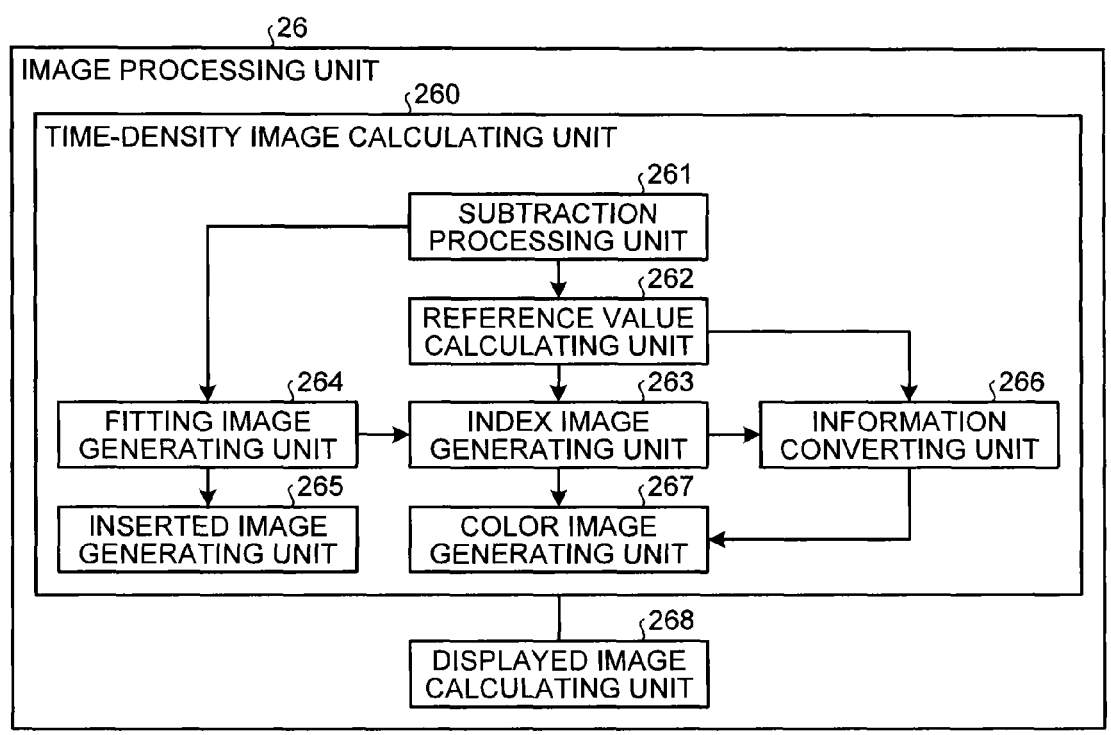
FIG. 2 is a diagram of an exemplary configuration of an image processing unit according to the first embodiment.

FIG. 2 is a diagram of an exemplary configuration of the image processing unit 26 according to the first embodiment. As shown in FIG. 2, the image processing unit 26 according to the first embodiment includes a time-density image calculating unit 260 and a displayed image calculating unit 268. The time-density image calculating unit 260 includes, as shown in FIG. 2, a subtraction processing unit 261, a reference value calculating unit 262, an index image generating unit 263, a fitting image generating unit 264, an inserted image generating unit 265, an information converting unit 266, and a color image generating unit 267.

The subtraction processing unit 261 is configured to generate a difference image such as a DSA image. More specifically, the subtraction processing unit 261 generates the difference image (e.g., a DSA image) obtained by performing a subtraction process on a mask image taken in the state where no contrast material has been injected and a contrast image taken in the state where a contrast material has been injected. In this situation, the subtraction processing unit 261 generates a difference image for each of the frames taken at a predetermined frame rate during a predetermined image taking period. In other words, using the mask image, the subtraction processing unit 261 performs a subtraction process on each of a plurality of contrast images taken during the period of time when the contrast material is flowing. For example, the subtraction processing unit 261 generates the difference images, as described above, for before the treatment and after the treatment.

In this situation, the subtraction processing unit 261 uses one frame taken immediately prior to the injection of the contrast material as the mask image. As a result, it is possible to minimize errors that may occur in a position alignment process (called a registration) due to body movements. Further, the subtraction processing unit 261 performs a noise reducing process by using one or more image processing filters such as a moving average (smoothing) filter, a Gaussian filter, a median filter, and the like. In other words, the subtraction processing unit 261 performs a pre-processing process including a position misalignment correction and a noise removal on each of the plurality of groups of X-ray images chronologically taken while using the contrast material.

Further, the subtraction processing unit 261 is also configured to be able to resize images for the purpose of speeding up the processes in the following stages. As described in detail later, the processes performed in the following stages include processes performed for each of the pixels. For this reason, for example, the subtraction processing unit 261, at first, resizes the original number of pixels "1024×1024" to "256×256", before the processes described below are performed. In other words, by performing the processes with coarse pixels, it is possible to speed up the entire processes. It is also acceptable to execute processes on the original pixels "1024×1024" in the background while the operator is viewing the processing results from the processes performed with the coarse pixels in this manner, so that the processing results with the original number of pixels can be displayed. Further, it is also acceptable to perform the resizing process described above only in a region specified by the operator. With this arrangement, the subtraction processing unit 261 makes it possible to shorten the time it takes before the images can be observed.

The subtraction processing unit 261 is also able to reduce noise contained in the images by resizing the images. For example, the subtraction processing unit 261 generates a difference image obtained by resizing an image of which the number of pixels is "1024×1024" to an image of which the number of pixels is "256×256". With this arrangement, when the resolution is high, the noise expressed in one pixel is expressed in the same pixel as the one expressing other signals. It is therefore possible to average out random noise contained in the image. The term "frames" used in this situation refers to "images". The term "frame rate" refers to the quantity of frames taken per unit time period.

The reference value calculating unit 262 is configured to calculate reference values used for normalizing various types of information related to the injection of the contrast material (the flow of the contrast material). More specifically, with respect to each of the difference images before and after the treatment generated by the subtraction processing unit 261, the reference value calculating unit 262 calculates the reference values such as a contrast material injection start time ($C_{start}$) a contrast material injection end time ($C_{stop}$) a contrast material injection time period ($C_{duration}$: $C_{stop}-C_{start}$), a maximum value of the image density ($C_{max}$), an accumulated value of image density values ($C_{AUC}$), a contrast material mean transit time ($C_{MTT}$), and a slope up to a maximum intensity ($C_{slope}$).

Next, the injection of the contrast material will be explained. The contrast material may automatically be injected via the injector 30 shown in FIG. 1. However, in many situations, a contrast material is manually injected by a medical doctor. In those situations, for example, there is a possibility that the time periods from the start of an image taking process to the injection of a contrast material and the speeds at which the contrast material is injected may be different between the angiography image taking processes before and after the treatment. To cope with this situation, the flow of the contrast material is normalized by using the reference values calculated by the reference value calculating unit 262. As a result, for example, it becomes possible to accurately compare the difference images before and after the treatment with one another, even in that situation. Next, specifics of the processes performed by the reference value calculating unit 262 will be explained in detail.

Figure 3:
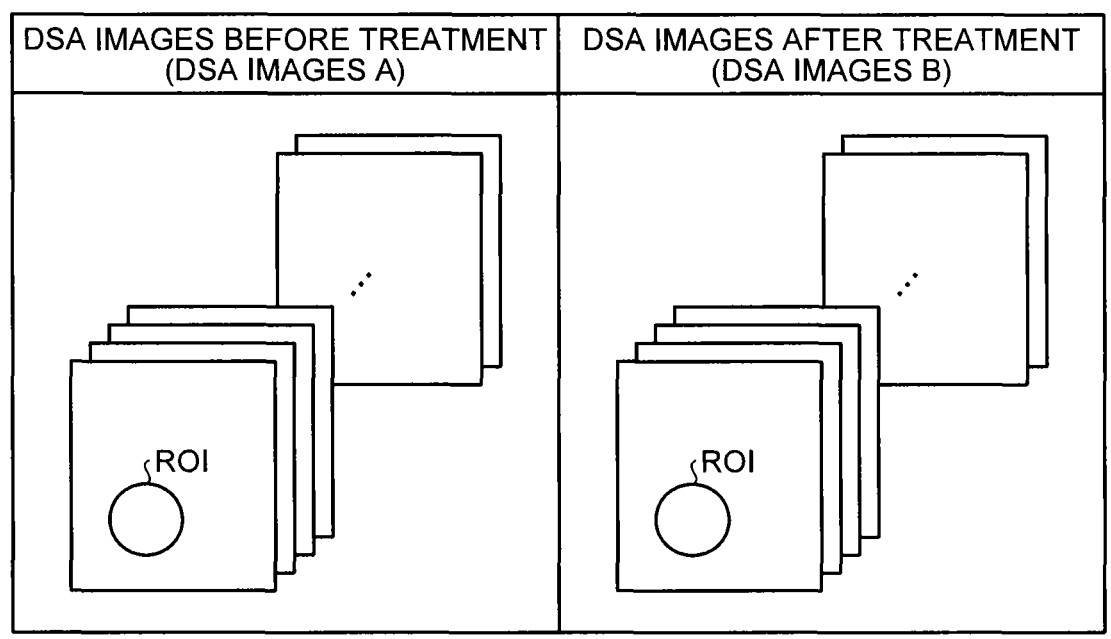
FIG. 3 is a drawing for explaining examples of difference images that serve as a processing target of a reference value calculating unit according to the first embodiment.

FIG. 3 is a drawing for explaining examples of difference images that serve as a processing target of the reference value calculating unit 262 according to the first embodiment. FIG. 3 illustrates DSA images before the treatment (hereinafter, "DSA images A") and DSA images after the treatment (hereinafter, "DSA images B") that are generated by the subtraction processing unit 261. For example, the DSA images A and the DSA images B serving as a processing target of the reference value calculating unit 262 each include a plurality of DSA images that are chronologically taken by using a predetermined image taking duration. In other words, the DSA images A and the DSA images B are configured so as to indicate, when the plurality of DSA images are displayed successively, the manner in which the contrast material flows before the treatment and after the treatment, i.e., the structures of the blood vessels, and the states of the blood flow. In the first embodiment, the example is explained in which the DSA images before and after the treatment are used; however, possible embodiments are not limited to this example. It is acceptable to use, for example, DSA images that are taken before and after an administration of a drug.

The reference value calculating unit 262 calculates the reference values used for normalizing the flow of the contrast material on the basis of a chronological transition of the signal intensity of the contrast material in a predetermined region, for each of the plurality of groups of X-ray images chronologically taken while using the contrast material. For example, as shown with the DSA images A and the DSA images B in FIG. 3, the reference value calculating unit 262 calculates each of the reference values on the basis of the chronological transition of the signal intensity of the contrast material in a Region Of Interest (ROI) that is set in an arbitrary position. In this situation, the ROI is set in an arbitrary position of the image or in a position where only an artery is present. The ROI may arbitrarily be set by a medical doctor. Alternatively, an artery may be detected by using an analysis application or the like, so that the ROI is automatically set on the detected artery.

Figure 4:
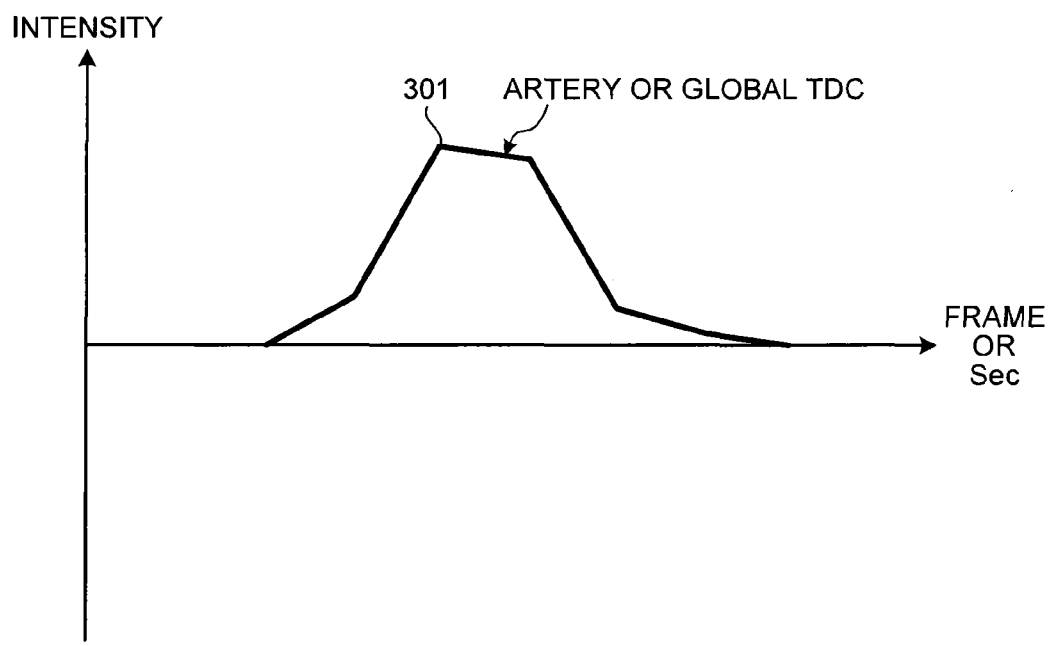
FIG. 4 provides charts for explaining exemplary processes performed by the reference value calculating unit according to the first embodiment.
Figure 4:
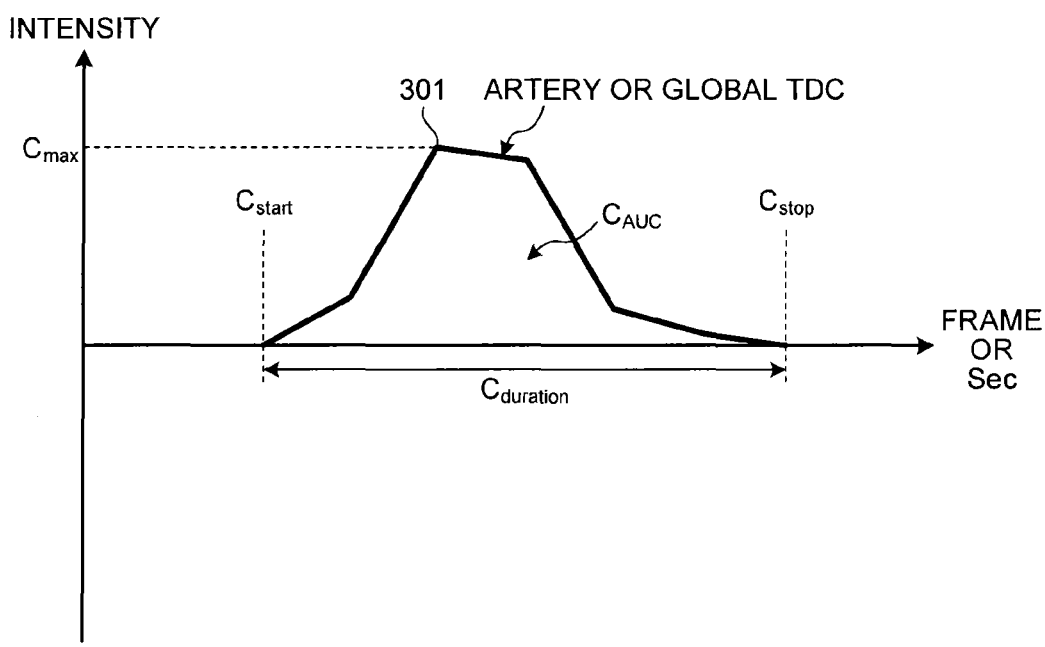

For example, the reference value calculating unit 262 generates a Time-Density Curve (TDC) on the basis of pixel values of the pixels contained in the ROI. After that, the reference value calculating unit 262 calculates the reference values by using the generated TDC. FIG. 4 provides charts for explaining exemplary processes performed by the reference value calculating unit 262 according to the first embodiment. In FIG. 4, the horizontal axis expresses frames or time, whereas the vertical axis expresses the intensity. For example, the reference value calculating unit 262 generates, as shown in FIG. 4(A), either an artery TDC or a global TDC for the DSA images A and for the DSA images B generated by the subtraction processing unit 261.

In this situation, the artery TDC is a TDC generated by using an average value of the pixel values of the pixels contained in a ROI set in a position within the image where only an artery is present. In contrast, the global TDC is a TDC generated by using an average value of the pixel values of the pixels contained in a ROI set in an arbitrary position within the image. In other words, with respect to each of the chronologically-taken frames that are contained in the DSA images A, the reference value calculating unit 262 calculates an average value of the pixel values of the pixels contained in the set ROI. After that, the reference value calculating unit 262 generates the TDC as shown in FIG. 4(A) in which the calculated average value for each of the frames is expressed on the vertical axis. The reference value calculating unit 262 also generates a TDC for the DSA images B in a similar manner. Because the global TDC includes regions other than the region of an artery, it is preferable to use the artery TDC when the user wishes to understand the injection state of a contrast material more accurately.

After that, the reference value calculating unit 262 calculates the various types of reference values, on the basis of the generated TDCs. First, an example of calculating the contrast material injection start time ($C_{start}$) will be explained. For example, the reference value calculating unit 262 calculates the contrast material injection start time ($C_{start}$) by using a method in one of the following three patterns. In a first pattern, the reference value calculating unit 262 extracts a frame in which the average intensity value on the TDC is equal to "X"% of a maximum value 301 and calculates the time of the extracted frame as the contrast material injection start time ($C_{start}$). In other words, in the first pattern, the reference value calculating unit 262 calculates the rising point of the TDC waveform as the contrast material injection start time ($C_{start}$). In this situation, the value "X" may arbitrarily be set by the operator such as a medical doctor or a designer.

In a second pattern, the reference value calculating unit 262 extracts frames in which, within the ROI, the ratio of such pixels of which the pixel value is equal to or larger than a predetermined threshold value "a" to all the pixels is "Y"% or larger, and calculates the earliest time in the time series among the extracted frames as the contrast material injection start time ($C_{start}$). In other words, in the second pattern, the reference value calculating unit 262 calculates the point in time at which the number of pixels visualized by the contrast material becomes equal to or larger than the certain value as the contrast material injection start time ($C_{start}$). In this situation, the values "a" and "Y" may arbitrarily be set by the operator such as a medical doctor or a designer.

Further, in a third pattern, when the contrast material is injected by using the injector 30 instead of being manually injected, the reference value calculating unit 262 obtains a signal indicating the start of the contrast material injection and being transmitted by the system controlling unit 21 and calculates the time indicated by the obtained signal as the contrast material injection start time ($C_{start}$).

Next, an example of calculating the contrast material injection end time ($C_{stop}$) will be explained. For example, the reference value calculating unit 262 calculates the contrast material injection end time by using a method in one of the following two patterns. In a first pattern, the reference value calculating unit 262 extracts a frame in which the average intensity value is equal to "Z"% of the maximum value 301, from among the frames later than the maximum value 301 in the time series and calculates the time of the extracted frame as the contrast material injection end time ($C_{stop}$). In other words, in the first pattern, the reference value calculating unit 262 calculates the falling point of the TDC waveform as the contrast material injection end time ($C_{stop}$). The value "Z" may arbitrarily be set by the operator such as a medical doctor or a designer.

In a second pattern, when the contrast material is injected by using the injector 30 instead of being manually injected, the reference value calculating unit 262 obtains a signal indicating the end of the contrast material injection and being transmitted by the system controlling unit 21 and calculates the time indicated by the obtained signal as the contrast material injection end time ($C_{stop}$).

After that, as shown in FIG. 4(B), the reference value calculating unit 262 calculates other reference values by using "$C_{start}$" and "$C_{stop}$" calculated as described above. In FIG. 4(B), an example in which both "$C_{start}$" and "$C_{stop}$" were calculated by using the first patterns will be explained. For example, as shown in FIG. 4(B), the reference value calculating unit 262 calculates "$C_{stop}-C_{start}$" as the contrast material injection time period ($C_{duration}$). Further, as shown in FIG. 4(B), the reference value calculating unit 262 calculates the intensity at the maximum value 301 on the TDC as the maximum value of the image density ($C_{max}$). In addition, as shown in FIG. 4(B), the reference value calculating unit 262 calculates the area of the TDC as an accumulated value of the image density values ($C_{AUC}$). In other words, the maximum value of the image density ($C_{max}$) and the accumulated value of the image density values ($C_{AUC}$) are each a value that reflects (e.g., a value that is proportional to) the density of the contrast material and the injection amount of the contrast material.

From each of the TDCs for the DSA images A and for the DSA images B, the reference value calculating unit 262 calculates the reference values described above. The patterns in which the contrast material injection start time ($C_{start}$)) and the contrast material injection end time ($C_{stop}$) are calculated may arbitrarily be selected by the operator.

Returning to the description of FIG. 2, for each of the plurality of groups of X-ray images, the index image generating unit 263 normalizes the flow of the contrast material at each of the pixels by using the reference values calculated by the reference value calculating unit 262 and further generates an image in which feature values of the normalized flow of the contrast material are reflected in each of the pixels. More specifically, the index image generating unit 263 normalizes the feature values of the signal intensities of the contrast material, by applying the reference values to the time-density curves each indicating the chronological transition of the signal intensity of the contrast material at a corresponding one of the pixels in each of the plurality of groups of X-ray images, so as to generate the image in which the normalized feature values are reflected in each of the pixels. For example, the index image generating unit 263 normalizes indices that functionally indicate a state of the blood flow by generating a TDC for each of the pixels that are the same among all the frames contained in the DSA images and applying the reference values thereto, so as to generate index images each of which is a functional image and in which the normalized index is reflected in each of the pixels.

In an example, by using the reference values calculated by the reference value calculating unit 262, the index image generating unit 263 normalizes indices as follows: a Peak Time (PT) that indicates a time period it takes for the pixel value to reach a maximum intensity at each of the pixels in the image; an Arrival Time (AT) which is a time period it takes for each of the pixels in the image to start being visualized by the contrast material; a Mean Width (MW) that indicates a half-value width of the peak on the TDC at each of the pixels in the image; a Peak Height (PH) at which the pixel value of each of the pixels in the image exhibits a maximum intensity value; an Area Under Curve (AUC) indicating the area of the TDC at each of the pixels in the image (the amount of contrast material that flowed into each of the pixels); a Wash Out (WT) indicating the time period from when the pixel value of each of the pixels in the image exhibits the maximum intensity value to when the contrast material has finished flowing out; a "slope" indicating the slope up to the maximum intensity on the TDC for each of the pixels in the image; and a Mean Transit Time (MTT) indicating an average passing time period of the contrast material. After that, the index image generating unit 263 generates index images (e.g., a PT image, an AT image, a MW image, a PH image, an AUC image, a WT image, a "slope" image, and/or an MTT image) in each of which the index values normalized for each of the pixels are reflected.

Figure 5:
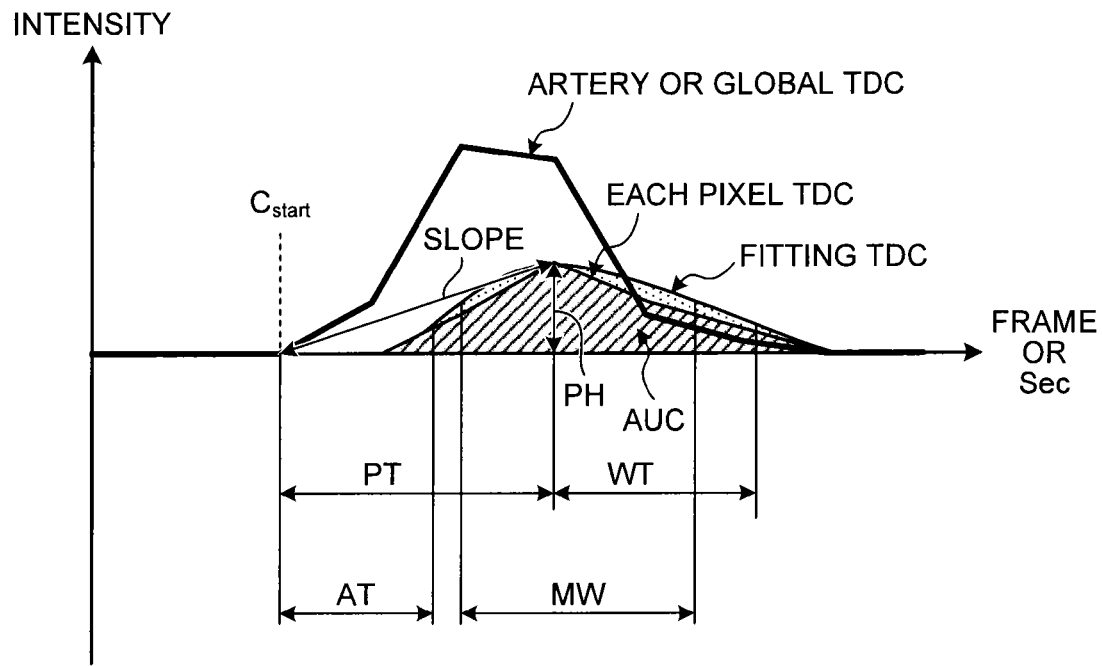
FIG. 5 is a chart for explaining an example of an index normalization process performed by an index image generating unit according to the first embodiment.

FIG. 5 is a chart for explaining an example of the index normalization process performed by the index image generating unit 263 according to the first embodiment. FIG. 5 illustrates an example in which the rising point in the waveform of either the artery TDC or the global TDC is calculated as the contrast material injection start time ($C_{start}$). Further, FIG. 5 illustrates an example in which the pieces of information are calculated at one pixel. In FIG. 5, the horizontal axis expresses frames or time, whereas the vertical axis expresses the intensity.

For example, for the DSA images A and the DSA images B, the index image generating unit 263 acquires the pixel values of the pixels in each of the frames and generates a TDC for each of the pixels that are in the same position among the different frames. In one example, the index image generating unit 263 generates a TDC for each of the pixels, as shown with "Each pixel TDC" in FIG. 5. After that, the index image generating unit 263 calculates the index values used for generating the index images described above, by performing the normalization process described below.

First, calculating the PT will be explained. As shown in FIG. 5, the index image generating unit 263 calculates, for each of the pixels, a time period or frames it takes for the pixel value to reach the maximum thereof since the "$C_{start}$" and determines the calculated value to be the PT of the pixel. By using the time period or the frames since the "$C_{start}$" in this manner, it is possible to calculate an accurate PT, even if the contrast material injection timing is different between the DSA images A and the DSA images B.

In this situation, the index image generating unit 263 calculates the time period or the frames since "$C_{start}$", by searching for the time or the frame at which a peak appears first (hereinafter, a "first-appearing peak" or a "first peak") while using two search directions: a chronologically forward direction and a chronologically backward direction. Because X-ray images overlap in the depth direction, a peak in an arterial phase and a peak in a venous phase may be displayed in mutually the same pixel. Accordingly, when the search is conducted while using the two search directions (i.e., the chronologically forward direction and the chronologically backward direction), the time or the frame exhibiting the first peak found in the search conducted in the chronologically forward direction prioritizes the artery phase, whereas the time or the frame exhibiting the first peak found in the search conducted in the chronologically backward direction prioritizes the venous phase. In other words, depending on which value is used for the generation of the PT image, it is possible to generate an image prioritizing the artery phase or an image prioritizing the venous phase.

Next, calculating the AT will be explained. As shown in FIG. 5, the index image generating unit 263 calculates, for each of the pixels, a time period or frames from the "$C_{start}$" to when the pixel starts being visualized and determines the calculated value to be the AT of the pixel. In this situation, the index image generating unit 263 determines the start of the visualization by using one of the following two methods. According to a first method, the index image generating unit 263 determines a time or a frame at which the pixel value exceeds "b"% of the "$C_{max}$" as the start of the visualization. According to a second method, the index image generating unit 263 determines a time or a frame at which the pixel value exceeds "c"% of the "PH" as the start of the visualization, where the "PH" is the maximum pixel value of the pixel.

Next, calculating the MW will be explained. As shown in FIG. 5, the index image generating unit 263 calculates, for each of the pixels, a time duration or frames from a rising point to a falling point each exhibiting a half value of the "PH". After that, the index image generating unit 263 determines a value obtained by dividing the value calculated for each of the pixels by the contrast material injection time period ($C_{duration}$) to be the MW of the pixel. By dividing the calculated value by the "$C_{duration}$" for each pixel in this manner, it is possible to calculate an accurate MW even if the contrast material injection time periods are different between the DSA images A and the DSA images B.

Next, calculating the PH will be explained. As shown in FIG. 5, the index image generating unit 263 calculates the maximum value on the TDC for each of the pixels. After that, the index image generating unit 263 determines a value obtained by dividing the value calculated for each of the pixels by the maximum value of the image density ($C_{max}$) to be the PH of the pixel. By dividing the calculated value by "$C_{max}$" for each pixel in this manner, it is possible to calculate an accurate PH, even if the densities of the injected contrast material are different between the DSA images A and the DSA images B. Further, the index image generating unit 263 searches for the peak while using the two search directions (i.e., the chronologically forward direction and the chronologically backward direction) and performs the process described above for each of the peaks found in the search. As a result, it is possible to generate an image prioritizing the arterial phase and an image prioritizing the venous phase.

Next, calculating the AUC will be explained. As shown in FIG. 5, the index image generating unit 263 calculates the area of the TDC for each of the pixels. After that, the index image generating unit 263 determines a value obtained by dividing the area size calculated for each of the pixels by the accumulated value of the image density values ($C_{AUC}$) to be the AUC of the pixel. By normalizing the calculated value with the reference value "$C_{AUC}$", it is possible to calculate an AUC, even if the injection amounts or the densities of the injected contrast material are different between the DSA images A and the DSA images B.

Next, calculating the WT will be explained. As shown in FIG. 5, the index image generating unit 263 calculates, for each of the pixels, a time period or frames between the "PH" and the time when the contrast material has finished flowing out and determines the calculated value to be the WT of the pixel. In this situation, the index image generating unit 263 determines the point in time at which the contrast material has finished flowing out, by using one of the following two methods. According to a first method, the index image generating unit 263 determines a time or a frame at which the pixel value has become lower than "b"% of the "$C_{max}$" to be the point in time at which the contrast material has finished flowing out. According to a second method, the index image generating unit 263 determines a time or a frame at which the pixel value becomes lower than "c"% of the "PH" to be the point in time at which the contrast material has finished flowing out.

Next, calculating the "slope" will be explained. As shown in FIG. 5, the index image generating unit 263 calculates PT/PH for each of the pixels. In this situation, because the PT and the PH are each normalized by using the reference values, it is possible to calculate an accurate "slope". Alternatively, the index image generating unit 263 may determine a value obtained by dividing the PT/PH value calculated for each of the pixels by the reference value "$C_{slope}$" to be the "slope" of the pixel.

Next, calculating the MTT will be explained. The index image generating unit 263 calculates, for each of the pixels, an MTT from the TDC by using a first moment method or the like. After that, the index image generating unit 263 determines a value obtained by dividing the MTT calculated for each of the pixels by the reference value "$C_{MTT}$" to be the MTT of the pixel.

As explained above, the index image generating unit 263 generates the TDC for each of the pixels for the DSA images A and the DSA images B and further calculates the PT, AT, MW, PH, AUC, WT, "slope", and MTT values that are normalized for each of the pixels. In other words, for the DSA images A and the DSA images B, the index image generating unit 263 generates an index image in which an index value is kept in correspondence with each of the pixels, for each of the various indices (e.g., PT, AT, MW, PH, AUC, WT, "slope", and MTT). In this situation, in the index images generated by the index image generating unit 263, because the index values are normalized by using the reference values as described above, it is possible to simply compare the index images between the DSA images A and the DSA images B.

During the index image generating process described above, the TDCs of the pixels are used. However, the X-ray diagnosis apparatus 100 according to the first embodiment may be configured so as to generate a fitting image and to use a TDC of the generated fitting image. In other words, the index image generating unit 263 may use a fitting TDC shown in FIG. 5. For example, when the TDC for each of the pixels is used, because spike noises that occur randomly may reach the maximum value, the position of the peak may be different from a true peak. Generating the fitting image makes it possible to address this situation.

Next, generating the fitting image will be explained. Returning to the description of FIG. 2, the fitting image generating unit 264 generates the fitting image by performing a curve fitting process on the images that were actually taken. In one example, the fitting image generating unit 264 generates the fitting image by performing a gamma fitting process expressed in the formula below, where "I" denotes the pixel value, "t" denotes a time, and "$t_0$" denotes a delay period (i.e., a time period from the start of the image taking process to the time of arrival of the contrast material).

$$I(t)=k(t-t_0)^\alpha \exp(-(t-t_0)/\beta)$$

In other words, the fitting image generating unit 264 determines coefficients "k", "α", and "β" that satisfy the formula above on the basis of the pixel value of each of the pixels. As a result, for example, it is possible to calculate the PT as "PT=αβ", and it is therefore possible to shorten the calculating process. The fitting image generating unit 264 performs the process described above for the DSA images A and for the DSA images B. In the example described above, the fitting image is generated by performing the gamma fitting process; however, possible embodiments are not limited to this example. For instance, the fitting image generating unit 264 may generate a fitting image by performing a moving average calculation or a spline interpolation on the images that were actually taken so as to perform a curve fitting process thereon.

Returning to the description of FIG. 2, the inserted image generating unit 265 generates an inserted image that is an image to realize an arbitrary frame rate, on the basis of the fitting image generated by the fitting image generating unit 264. The fitting image described above is obtained by performing the fitting process on plotted pixel values of the images that were actually taken at a predetermined frame rate, and the fitting image is configured to complement pixel values between plotted points. As a result, the inserted image generating unit 265 is able to generate images at an arbitrary frame rate (a time interval: Δt).

For example, if actual X-ray images are taken at 3 frames per second (fps), the inserted image generating unit 265 is able to generate virtual images while satisfying Δt=1/60 sec. As a result, the inserted image generating unit 265 is also able to generate a moving picture that shows the flow of the contrast material in slow motion. Alternatively, if actual X-ray images are taken at 3 fps, the inserted image generating unit 265 is also able to generate inserted images while satisfying Δt=1/3 sec, which is the same frame rate as the actual frame rate.

The information converting unit 266 converts the information about the signal intensities of the pixels in each of the plurality of X-ray images into color information used for expressing the flow of the contrast material while using colors. More specifically, the information converting unit 266 converts, for each of the indices, the information about the index at each of the pixels in each of the plurality of groups of X-ray images into an upper limit value and a lower limit value of the color information used for expressing the group of X-ray images in color. For example, on the basis of the index values of the index images calculated by the index image generating unit 263, the information converting unit 266 sets a range of a color bar used for expressing the index images in color. Next, setting a range of colors for each of the index images will be explained.

Figure 6:
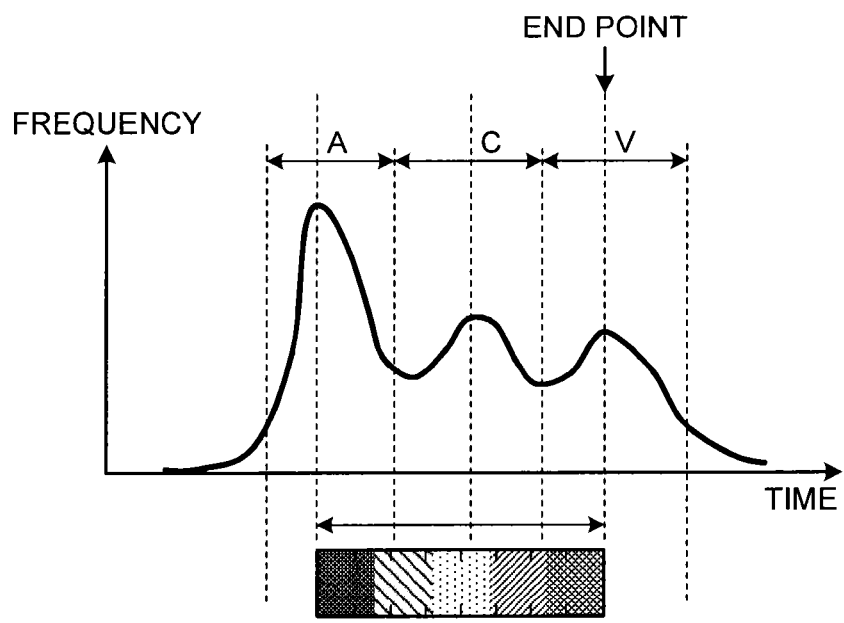
FIG. 6 is a drawing for explaining an example of a color bar end point setting process performed by an information converting unit according to the first embodiment.

First, setting colors to express the PT image in color will be explained. In the following sections, setting the colors by using color bars will be explained for the sake of convenience of the explanation. In this situation, the information converting unit 266 sets the "$C_{start}$" as the start point of a color bar. After that, the information converting unit 266 sets the end point of the color bar, on the basis of a frequency distribution of the PT values of the pixels. FIG. 6 is a drawing for explaining an example of the color bar end point setting process performed by the information converting unit 266 according to the first embodiment. In FIG. 6, the horizontal axis expresses "time", whereas the vertical axis expresses "frequency". The "time" in FIG. 6 signifies the "PT", whereas the "frequency" in FIG. 6 signifies the quantity of pixels having the PH value at that time.

For example, for the DSA images A and for the DSA images B, the information converting unit 266 generates frequency distribution data as shown in FIG. 6, by using the PT values of the pixels. After that, the information converting unit 266 searches for a peak from the later side on the time axis and sets the position of the first peak detected to be the end point of the color bar, as shown in FIG. 6. In this situation, the information converting unit 266 extracts the end point of the color bar for the DSA images A and for the DSA images B and sets one of the peak positions that is later in the time series as the eventual end point of the color bar. Thus, the information converting unit 266 has set the color bar used for expressing the PT images in color. As a result, the information converting unit 266 is able to set the color bar that is stable.

In this situation, as shown in FIG. 6, the information converting unit 266 divides the temporal region into three regions on the basis of peaks A, C, and V of the frequency distribution chart. The peaks A, C, and V shown in FIG. 6 are peaks caused by an arterial phase, an intermediate phase, and a venous phase. For example, the information converting unit 266 sets a region from the point in time at which the value is equal to "e"% of the value at the peak A, to the middle point between the peak A and the peak C, as a temporal region containing the peak A. Further, the information converting unit 266 sets the region between the peak A and the peak V as a temporal region containing the peak C. In addition, the information converting unit 266 sets a region from the middle point between the peak C and the peak V, to the point in time at which the value is equal to "f"% of the value at the peak V as a temporal region containing the peak V. As a result, the temporal region in the arterial phase, the temporal region in the intermediate phase, and the temporal region in the venous phase have been set. Thus, by repeatedly playing back only the images contained in each of the temporal regions, it is possible to easily display dynamics of the blood flow in each of the phases as a moving picture. In this situation, the intermediate phase corresponds to a location between the artery and the venous and includes a capillary phase in which the contrast material passes through capillaries and a temporal phase in which the contrast material permeates tissues (intercellular spaces) in the surroundings of the capillaries. Alternatively, the dividing of the temporal region based on the frequency distribution described above may be performed by the index image generating unit 263.

Next, setting a color bar used for expressing the AT image or the MW image in color will be explained. In that situation, the information converting unit 266 extracts the AT values or the MW values of the pixels from the DSA images A and from the DSA images B. After that, the information converting unit 266 compares the smallest value from the DSA images A with the smallest value from the DSA images B and sets the smaller of the two values as the start point of the color bar. In addition, the information converting unit 266 compares the largest value from the DSA images A with the largest value from the DSA images B and sets the larger of the two values as the end point of the color bar.

Next, setting a color bar used for expressing the PH image, the AUC image, or the "slope" image in color will be explained. In that situation, the information converting unit 266 sets the start point of the color bar to "0". After that, the information converting unit 266 extracts the PH values, the AUC values, or the "slope" values of the pixels from the DSA images A and from the DSA images B. Further, the information converting unit 266 compares the largest value from the DSA images A with the largest value from the DSA images B and sets the larger of the two values as the end point of the color bar.

In the examples described above, the upper limit and the lower limit of the colors are set with the peaks of the frequency distribution of the index values or with the index values. However, possible embodiments are not limited to these examples. For example, an upper limit and a lower limit of the colors may be set, in advance, with time or with numerical values in a fixed manner. For example, the information converting unit 266 may set, in advance, an upper limit and a lower limit of the colors with the time expressed on the horizontal axis of the frequency distribution chart shown in FIG. 6.

Returning to the description of FIG. 2, the color image generating unit 267 is configured to generate a color image on the basis of the color information resulting from the conversion by the information converting unit 266. For example, the color image generating unit 267 assigns colors in the range of the color bar set by the information converting unit 266 and expresses, in color, the index images generated by the index image generating unit 263 on the basis of the assigned colors. For example, the color image generating unit 267 assigns colors to the color bar so that the arterial phase corresponds to red, the venous phase corresponds to blue, and the intermediate phase (the capillary phase) corresponds to green, and generates the color images on the basis of the assigned colors.

Figure 7:
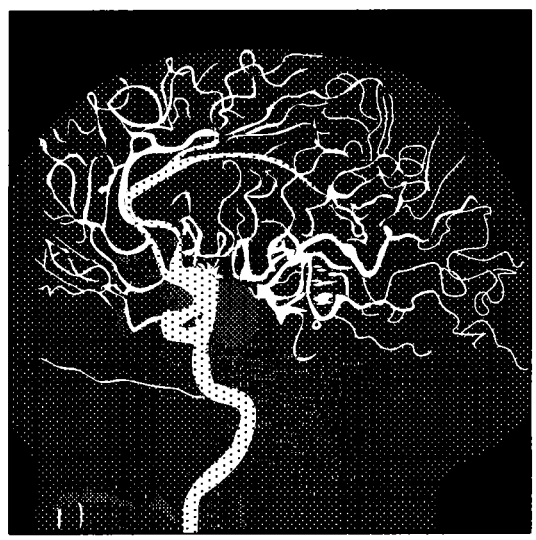
FIG. 7 is a drawing of examples of color images generated by a color image generating unit according to the first embodiment.

FIG. 7 is a drawing of examples of the color images generated by the color image generating unit 267 according to the first embodiment. FIG. 7 illustrates a PT image expressed in color. For example, as shown in FIG. 7, the color image generating unit 267 generates a color image in which, to each of the pixels in the PT image, a color corresponding to the PT value of the pixel is assigned, on the basis of the color bar to which colors have been assigned. In other words, the color image generating unit 267 generates the color image in which "red" is assigned to such pixels to which the contrast material has reached quickly and which took a short period of time to reach the peak (PT), whereas "green" or "blue" is assigned to such pixels that took a longer period of time to reach the peak. The color image generating unit 267 assigns the colors to the index images generated from the DSA images A and the DSA images B on the basis of mutually the same color bar so as to generate respective color images.

For each of the index images other than the PT image, the color image generating unit 267 assigns colors to the color bar for the indices set by the information converting unit 266 in the same manner as described above. After that, the color image generating unit 267 generates color images in which the pixels in the index images generated by the index image generating unit 263 are colored on the basis of the color bars.

Figure 8:
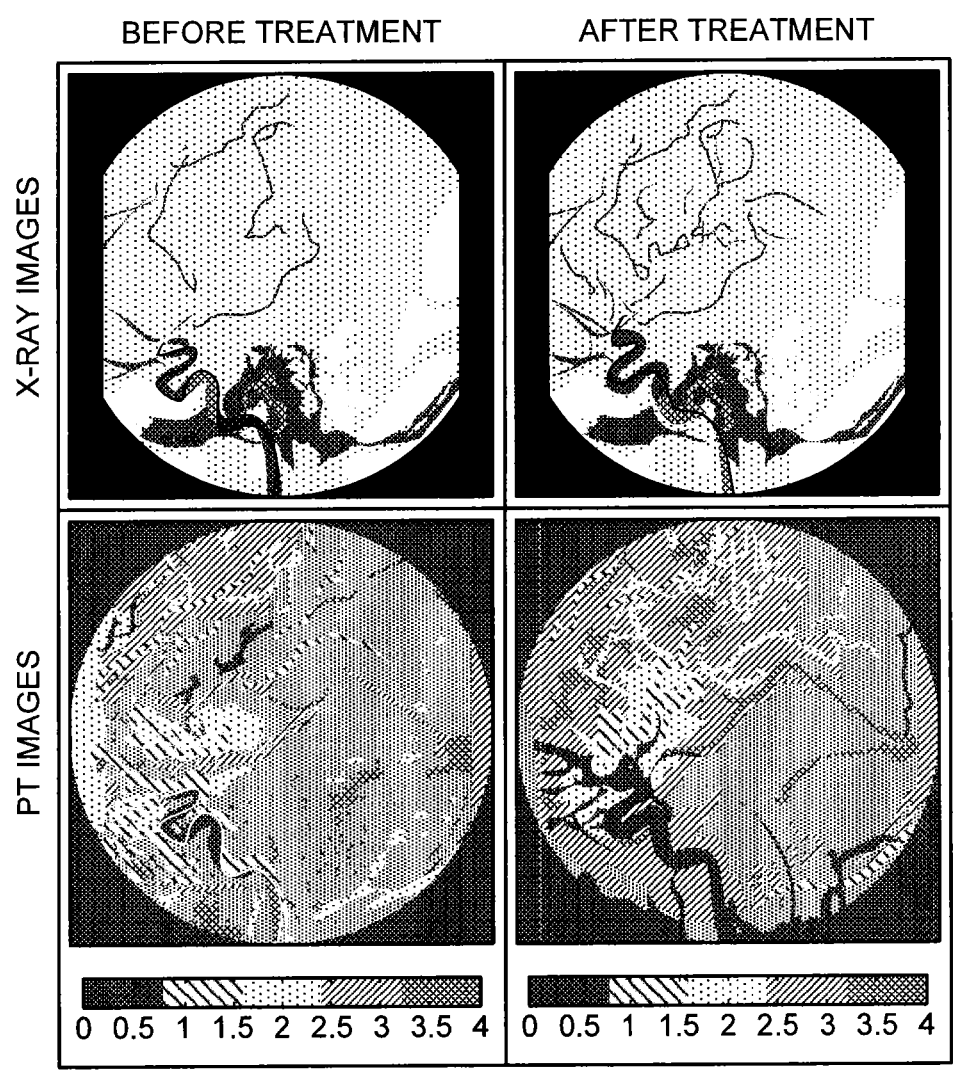
FIG. 8 is a drawing of an example of a positional arrangement of images realized by a displayed image calculating unit according to the first embodiment.

Returning to the description of FIG. 2, the displayed image calculating unit 268 is configured to perform a processing process and a positional arrangement process for the purpose of causing the display unit 23 to display the color images generated by the color image generating unit 267. FIG. 8 is a drawing of an example of a positional arrangement of images realized by the displayed image calculating unit 268 according to the first embodiment. For example, as shown in FIG. 8, the displayed image calculating unit 268 arranges four images, namely, X-ray images (monochrome images) before and after a treatment and PT images before and after the treatment. The positional arrangement of the images shown in FIG. 8 is merely an example. Alternatively, for instance, it is possible to arbitrarily arrange four images by combining DSA images before and after a treatment with various index images before and after the treatment.

Figure 9:
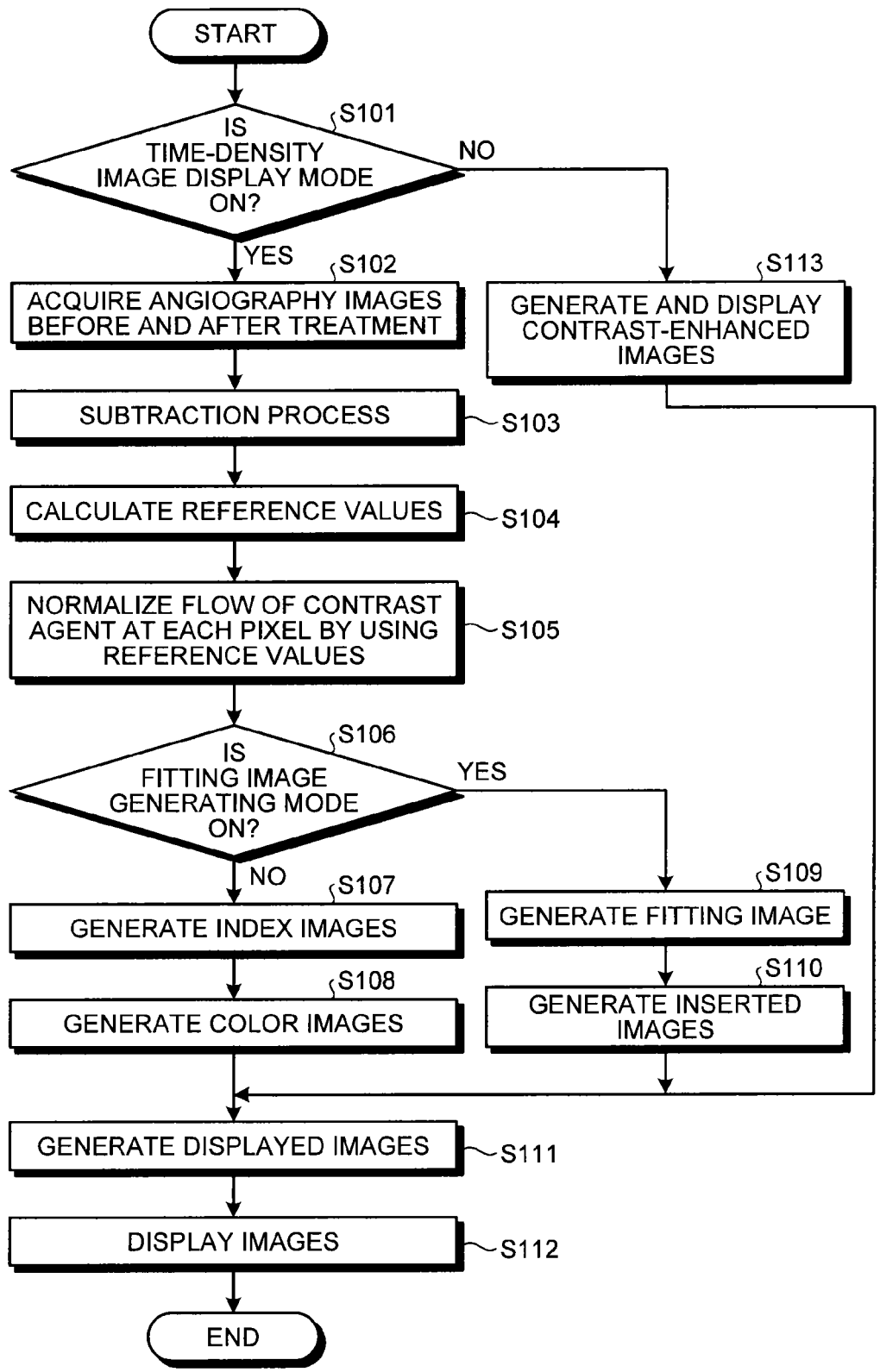
FIG. 9 is a flowchart of a procedure in a process performed by the X-ray diagnosis apparatus according to the first embodiment.

Next, a process performed by the X-ray diagnosis apparatus 100 according to the first embodiment will be explained, with reference to FIG. 9. FIG. 9 is a flowchart of a procedure in the process performed by the X-ray diagnosis apparatus 100 according to the first embodiment. As shown in FIG. 9, in the X-ray diagnosis apparatus 100 according to the first embodiment, when the time-density image display mode is on (step S101: Yes), the subtraction processing unit 261 acquires angiography images before and after a treatment (step S102) and performs the subtraction process (step S103).

After that, the reference value calculating unit 262 calculates reference values for each of the angiography images before and after the treatment on which the subtraction process was performed by the subtraction processing unit 261 (step S104). Subsequently, the index image generating unit 263 normalizes the flow of the contrast material at each of the pixels by using the reference values (step S105). After that, the fitting image generating unit 264 judges whether the fitting image generating mode is on (step S106). If the fitting image generating mode is not on (step S106: No), the index image generating unit 263 generates index images (step S107).

On the contrary, if the fitting image generating mode is on (step S106: Yes), the fitting image generating unit 264 generates a fitting image (step S109), so that the index image generating unit 263 generates index images on the basis of the fitting image generated by the fitting image generating unit 264 (step S107). When the fitting image has been generated, one or more inserted images may be generated by the inserted image generating unit 265 (step S110).

When the index images are generated at step S107, the information converting unit 266 sets the range of color bars, so that the color image generating unit 267 generates color images on the basis of the color bars (step S108). After that, the displayed image calculating unit 268 generates displayed images (step S111), so that the display unit 23 displays the images (step S112). If the time-density image display mode is not on (step S101: No), the X-ray diagnosis apparatus 100 generates and displays contrast-enhanced images (step S113).

As explained above, according to the first embodiment, the reference value calculating unit 262 calculates the reference values used for normalizing the flow of the contrast material, on the basis of the chronological transition of the signal intensity of the contrast material in the predetermined region, for each of the plurality of groups of X-ray images chronologically taken while using the contrast material. For each of the plurality of groups of X-ray images, the index image generating unit 263 normalizes the flow of the contrast material at each of the pixels by using the reference values calculated by the reference value calculating unit 262 and generates the index images in which the feature values of the normalized flow of the contrast material are reflected in each of the pixels. The displayed image calculating unit 268 causes the display unit 23 to display the images generated by the index image generating unit 263. Consequently, the X-ray diagnosis apparatus 100 according to the first embodiment is able to display the flows of the contrast material in the mutually-different angiography images in a normalized manner and thus makes it possible to improve the visibility of the angiography images.

Further, according to the first embodiment, the information converting unit 266 converts, for each of the indices, the information about the index at each of the pixels in each of the plurality of groups of X-ray images into the upper limit value and the lower limit value of the color information used for expressing the group of X-ray images in color. The color image generating unit 267 expresses the images generated by the index image generating unit 263 in color, by using the color information resulting from the conversion by the information converting unit 266. Consequently, the X-ray diagnosis apparatus 100 according to the first embodiment is able to cause the angiography images to be displayed while being expressed in color by using the normalized indices and thus makes it possible to improve the visibility of the angiography images.

Further, according to the first embodiment, the fitting image generating unit 264 generates the fitting TDC by performing the fitting process on each of the time-density curves of the pixels in each of the plurality of X-ray images. Consequently, the X-ray diagnosis apparatus 100 according to the first embodiment makes it possible to reduce impact of noises.

Furthermore, according to the first embodiment, the reference value calculating unit 262 calculates the contrast material injection start time, the contrast material injection time period, the maximum value of the image density, and the accumulated value of the image density values, as the reference values. Consequently, the X-ray diagnosis apparatus 100 according to the first embodiment is able to normalize the various types of index images and thus makes it possible to accurately analyze the dynamics of the blood flow.

Further, according to the first embodiment, when the contrast material is injected into the subject by using the injector 30, the reference value calculating unit 262 obtains the contrast material injection start time and the contrast material injection time period from the injector 30. Consequently, the X-ray diagnosis apparatus 100 according to the first embodiment makes it possible to reduce the load related to the calculation of the various types of information when the injector 30 is used.

Furthermore, according to the first embodiment, each of the plurality of X-ray images is either an image showing a state where the contrast material has been injected or an image obtained by subtracting an image taken immediately prior to the injection of the contrast material from each of the images showing the state where the contrast material has been injected. Accordingly, the X-ray diagnosis apparatus 100 according to the first embodiment makes it possible to reduce errors in the position alignment process.

Further, according to the first embodiment, when the plurality of X-ray images of which the contrasts are enhanced at mutually-different times are to be compared with one another, the reference value calculating unit 262 calculates the contrast material injection start times in such a manner that the contrast material injection start times are substantially the same among the plurality of groups of X-ray images. Consequently, the X-ray diagnosis apparatus 100 according to the first embodiment makes it possible to easily compare and analyze the X-ray images before and after a treatment.

Further, according to the first embodiment, the index image generating unit 263 normalizes the feature values of the signal intensities of the contrast material, by applying the reference values to the time-density curves of the pixels in each of the plurality of groups of X-ray images. In addition, the information converting unit 266 sets, for each of the feature values of the signal intensities, the upper limit value and the lower limit value of the color information used for expressing the groups of X-ray images in color by using the feature value of the signal intensity normalized by the index image generating unit 263. Consequently, the X-ray diagnosis apparatus 100 according to the first embodiment makes it possible to accurately analyze the dynamics of the blood flow, by generating the color images that accurately reflect the features of the signal intensities of the contrast material reflecting the dynamics of the blood flow.

Further, according to the first embodiment, to bring the signal intensity maximum time period, which is the time period it takes for the signal intensity to reach the maximum thereof and serves as a feature value of the signal intensity, into correspondence with each of the pixels, the index image generating unit 263 extracts the first peak from the plurality of X-ray images by searching in the chronologically forward direction and in the chronologically backward direction and brings one of the two extracted first peaks into correspondence with the pixel as the signal intensity maximum time period. Consequently, the X-ray diagnosis apparatus 100 according to the first embodiment makes it possible to arbitrarily select and display the image that prioritizes one of the arterial and venous phases.

Furthermore, according to the first embodiment, when the signal intensity maximum time period, which is the time period it takes for the signal intensity to reach the maximum thereof, is used as a feature value of the signal intensity, the index image generating unit 263 extracts the peaks corresponding to the arterial, the intermediate, and the venous phases on the basis of the frequency distribution of the signal intensity maximum time periods of the pixels, and further classifies the plurality of X-ray images chronologically taken, into the arterial phase, the intermediate phase, and the venous phase on the basis of the extracted peaks. After that, the displayed image calculating unit 268 displays each of the X-ray images classified by the index image generating unit 263. Consequently, the X-ray diagnosis apparatus 100 according to the first embodiment is able to cause the moving picture of only the arterial phase, only the intermediate phase, or only the venous phase to be displayed and thus makes it possible to perform the analysis more easily. For example, the X-ray diagnosis apparatus 100 makes it possible to perform a detailed analysis more easily by generating and displaying an index image for each of the temporal regions corresponding to the arterial phase, the intermediate phase (e.g., the capillary phase), and the venous phase. In one example, the X-ray diagnosis apparatus 100 generates and displays PT images each of which corresponds to only the intermediate phase of the DSA images A and of the DSA images B before and after a treatment.

Furthermore, according to the first embodiment, when the signal intensity maximum time period, which is the time period it takes for the signal intensity to reach the maximum thereof, is used as a feature value of the signal intensity, the information converting unit 266 generates the frequency distribution data of the signal intensity maximum time period for each of the pixels, extracts the peak corresponding to either the venous phase or the intermediate phase on the basis of the generated frequency distribution data, and sets the time at which the extracted venous phase or the extracted intermediate phase appears as the upper limit value. Consequently, the X-ray diagnosis apparatus 100 according to the first embodiment makes it possible to set the stable color range.

Furthermore, according to the first embodiment, the color image generating unit 267 extracts the arterial phase, the intermediate phase, and the venous phase from the X-ray images on the basis of the signal intensity maximum time period, which is the time period it takes for the signal intensity to reach the maximum thereof, and further expresses the extracted arterial, intermediate, and venous phases in color so as to be in mutually-different colors. Consequently, the X-ray diagnosis apparatus 100 according to the first embodiment makes it possible for the viewer to observe the blood flow in the images more easily.

Furthermore, according to the first embodiment, when a plurality of X-ray images showing blood vessels with enhanced contrast are to be compared with one another, the displayed image calculating unit 268 causes the plurality of X-ray images and the color images each of which is generated from a different one of the plurality of X-ray images to be displayed side by side. Consequently, the X-ray diagnosis apparatus 100 according to the first embodiment makes it possible to provide the angiography images taken at the mutually-different time periods in such a manner that it is easier to compare the images with one another.

Further, according to the first embodiment, the inserted image, which is the image to realize the arbitrary frame rate, is generated by using the fitting TDC generated by the fitting image generating unit 264. Consequently, the X-ray diagnosis apparatus 100 according to the first embodiment makes it possible to easily generate images in slow motion, for example.

Furthermore, according to the first embodiment, the subtraction processing unit 261 performs the pre-processing process including the position misalignment correction and the noise removal related to the movement of the subject, on each of the plurality of groups of X-ray image chronologically taken while using the contrast material. Consequently, the X-ray diagnosis apparatus 100 according to the first embodiment makes it possible to display the angiography images that are easy to view.

In the first embodiment described above, the example is explained in which the color images each of which is related to a single index is generated and displayed. As a second embodiment, an example will be explained in which each color image is generated on the basis of a plurality of indices. In other words, in the second embodiment, specifics of the process performed by the color image generating unit 267 are different. The second embodiment will be explained below while a focus is placed on the difference.

Figure 10:
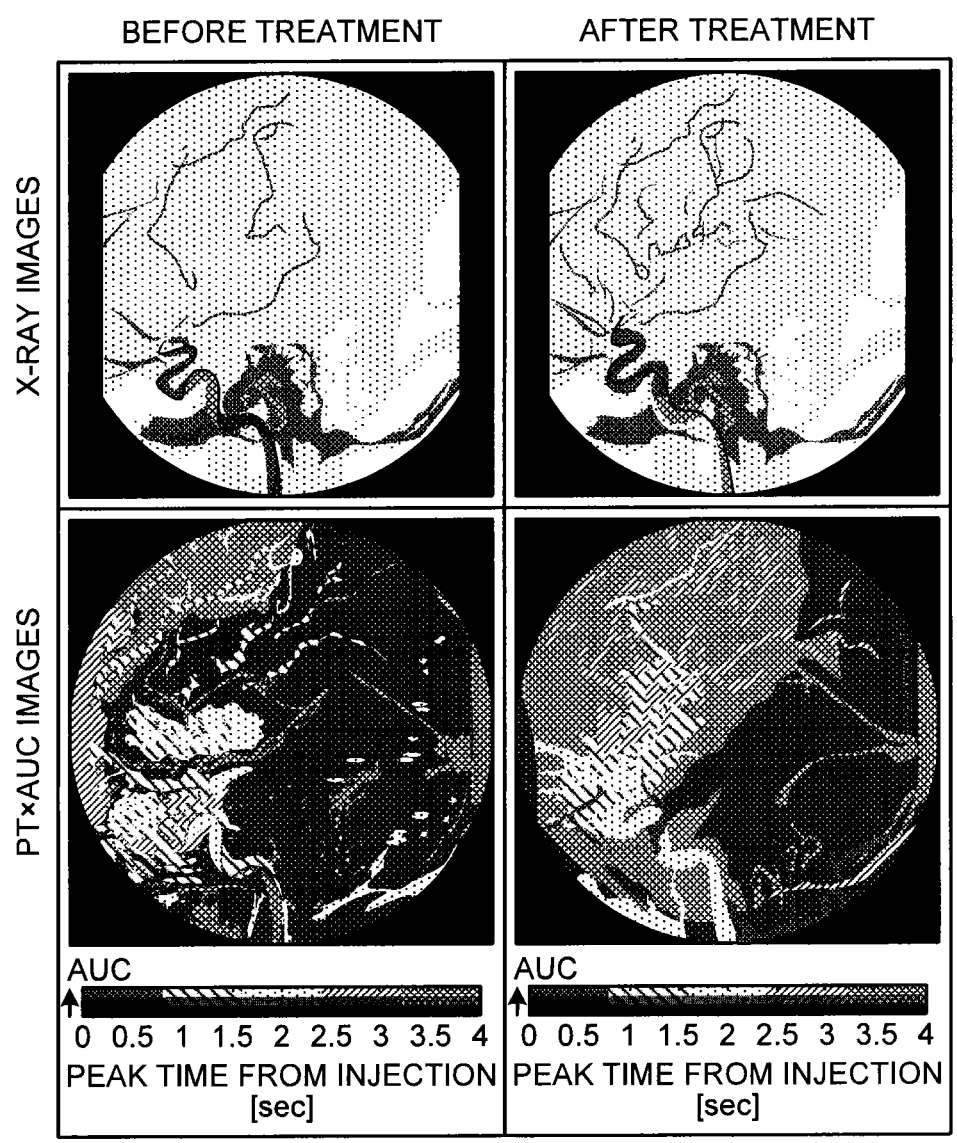
FIG. 10 is a drawing of examples of color images generated by a color image generating unit according to a second embodiment.

The color image generating unit 267 according to the second embodiment sets colors and an indicator for changing the state of the colors, on the basis of the plurality of indices. More specifically, from among the plurality of indices including the PT, the AUC, the AT, the MW, the PH, the WT, the "slope", and the MTT, the color image generating unit 267 selects two indices as indices of the signal intensity and further generates a color image in which one of the indices expresses the colors, whereas the other index expresses the indicator used for changing the state of the colors. In this situation, the color image generating unit 267 according to the second embodiment uses luminosity, chroma, or transparency as the indicator used for changing the state of the colors. In this situation, the transparency denotes transparency rates of the colors. FIG. 10 is a drawing of examples of color images generated by the color image generating unit 267 according to the second embodiment. FIG. 10 illustrates an example in which X-ray images before and after a treatment and color images before and after the treatment are displayed. Further, FIG. 10 illustrates the example in which the PT and the AUC are used as the indices, whereas the colors are assigned to the PT, while the luminosity is assigned to the AUC.

For example, as shown in FIG. 10, the color image generating unit 267 generates PT×AUC images each of which uses the PT and the AUC. In this situation, the color image generating unit 267 sets a color bar by expressing the PT on the horizontal axis and assigning the colors thereto and by expressing the AUC on the vertical axis and assigning the luminosity thereto. In other words, the color image generating unit 267 generates the color images in which the colors change in accordance with the PT time period expressed on the horizontal axis, whereas the luminosity changes in accordance with the value of the AUC expressed on the vertical axis. In this situation, the luminosity expressing the AUC on the vertical axis is set in such a manner that, as shown with the color bar in FIG. 10, the larger the AUC value is, the more luminous it is and the smaller the AUC value is, the less luminous it is. As a result, for example, it is possible to express an extremely small signal in terms of the AUC value (e.g., a signal close to noise) by arranging the corresponding PT value to be displayed dark with a low level of luminosity. Consequently, the noise component is rendered dark and becomes obscure. It is therefore possible to allow the viewer to observe other important signals. The example described above is merely an example. The color image generating unit 267 according to the second embodiment is able to generate color images by using any arbitrary combination of indices. In another example, the color image generating unit 267 may generate PT×PH images. In that situation, the color image generating unit 267 generates color images in which the colors change in accordance with the PT time period expressed on the horizontal axis, whereas an indicator for luminosity or the like changes in accordance with the value of the PT expressed on the vertical axis.

As described above, according to the second embodiment, from among the plurality of indices including the PT, the AUC, the AT, the MW, the PH, the WT, the "slope", and the MTT, the color image generating unit 267 selects two indices as the indices of the signal intensity and further generates the color images in which one of the two selected indices expresses the colors, whereas the other index expresses the indicator used for changing the state of the colors. Consequently, the X-ray diagnosis apparatus 100 according to the second embodiment makes it possible to further improve the visibility by using the indices in a combined manner. For example, by generating the PT×AUC images, the X-ray diagnosis apparatus 100 is able to eliminate the noise components and thus makes it possible to provide the images that are easier to view.

In the first and the second embodiments described above, the examples are explained in which the X-ray images (the monochrome images) and the color images are displayed separately. In a third embodiment, an example will be explained in which X-ray images and color images are displayed in a superimposed manner. In other words, in the third embodiment, specifics of the process performed by the displayed image calculating unit 268 are different. The third embodiment will be explained below, while a focus is placed on the difference.

Figure 11:
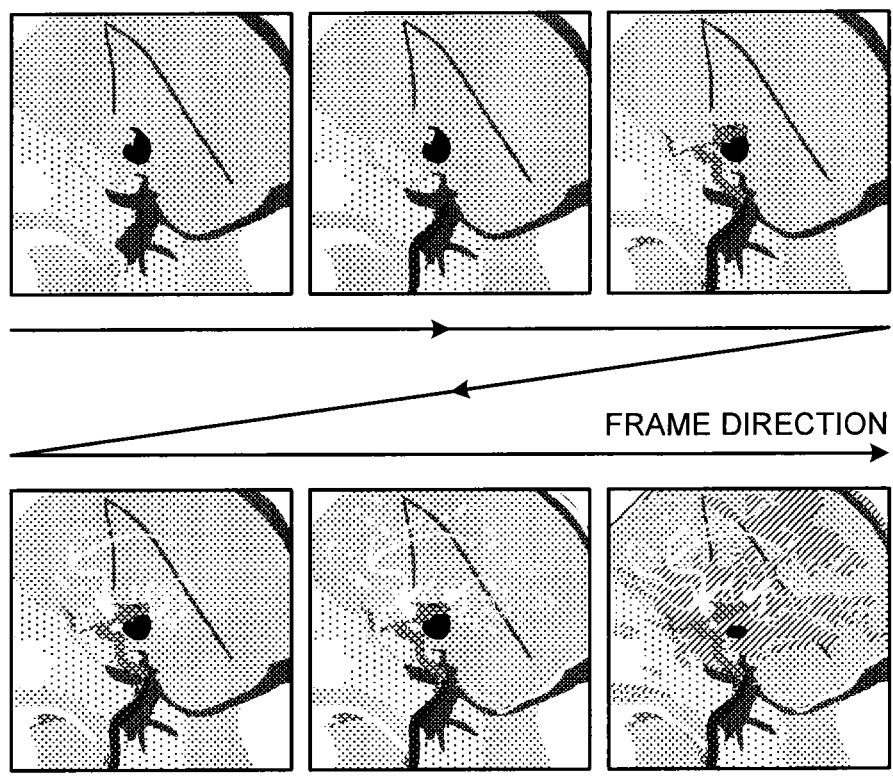
FIG. 11 is a drawing of examples of displayed images generated by a displayed image calculating unit according to a third embodiment.

The displayed image calculating unit 268 according to the third embodiment causes the color images generated by the color image generating unit 267 and X-ray images to be displayed in a superimposed manner. FIG. 11 is a drawing of examples of displayed images generated by the displayed image calculating unit 268 according to the third embodiment. FIG. 11 illustrates the examples in which the color images are PT images. For example, as shown in FIG. 11, the displayed image calculating unit 268 generates displayed images in which, while an X-ray moving picture is displayed at first, the pixels that have reached a peak time (PT) are sequentially rendered in color. With this arrangement, it is possible to display the manner in which the monochrome X-ray images are gradually turned into color images in a dynamic manner. This arrangement thus enables the viewer to better understand the dynamics of the blood flow.

Figure 12:
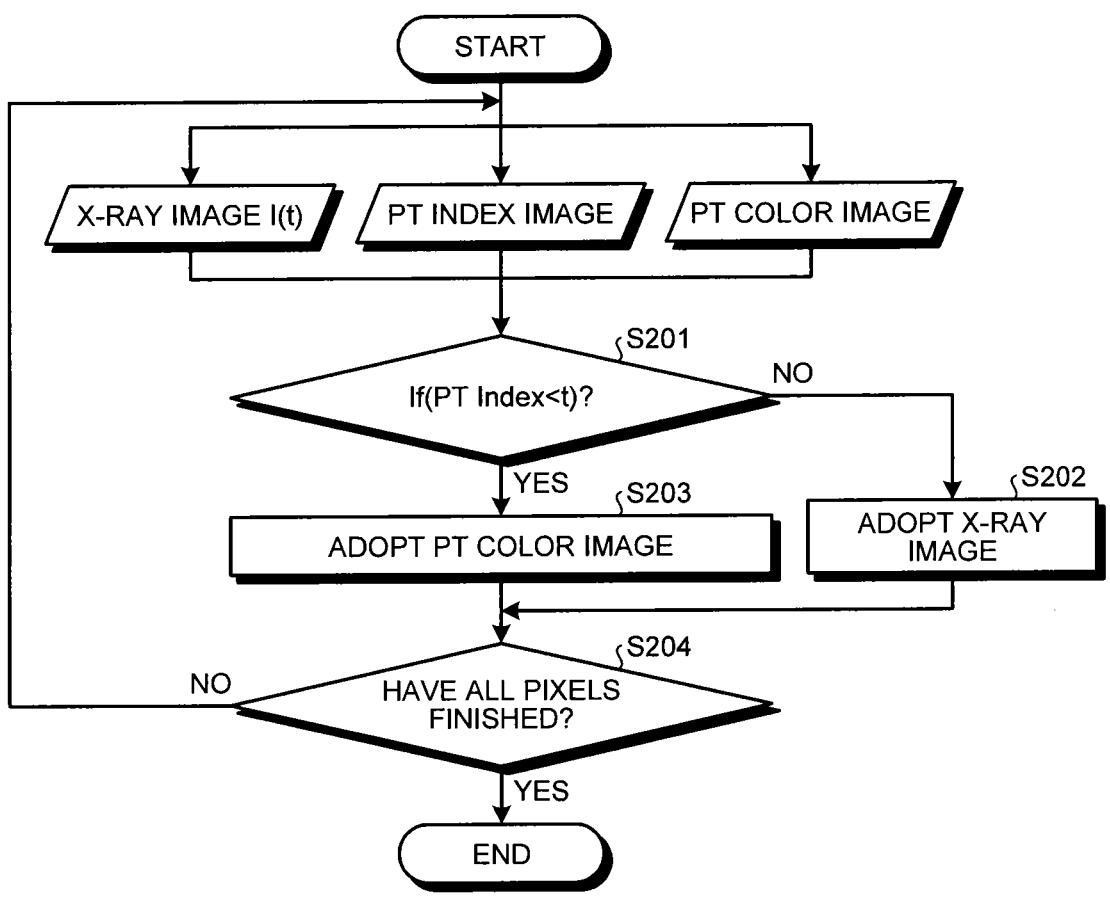
FIG. 12 is a flowchart of a procedure in a process performed by an X-ray diagnosis apparatus according to the third embodiment.

Next, a procedure in a process performed by the X-ray diagnosis apparatus 100 according to the third embodiment will be explained, with reference to FIG. 12. FIG. 12 is a flowchart for explaining the procedure in the process performed by the X-ray diagnosis apparatus 100 according to the third embodiment. As shown in FIG. 12, the displayed image calculating unit 268 extracts an X-ray moving picture, an index image of which the index is the PT (a PT Index image), and a color image of the PT index image (a PT color image) and judges whether the time of the moving picture has exceeded the PT time value for each of the pixels contained in the PT index image (step S201).

In this situation, if the time has not exceeded the PT time value for each of the pixels contained in the PT index image (step S201: No), the displayed image calculating unit 268 adopts the X-ray image (step S202). On the contrary, if the time has exceeded the PT time value for each of the pixels contained in the PT index image (step S201: Yes), the displayed image calculating unit 268 adopts the PT color image in which the pixels that have reached the PT value are rendered in color (step S203).

After that, the displayed image calculating unit 268 judges whether all the pixels have reached the PT value (step S204). If not all the pixels have reached the PT value (step S204: No), the displayed image calculating unit 268 returns to step S201 and continues the process. On the contrary, if all the pixels have reached the PT value (step S204: Yes), the displayed image calculating unit 268 ends the process.

As explained above, according to the third embodiment, the displayed image calculating unit 268 causes the color images generated by the color image generating unit 267 to be displayed while being superimposed on the X-ray images. Consequently, the X-ray diagnosis apparatus 100 according to the third embodiment makes it possible to provide the images in which the dynamics of the blood is easy to view.

The first to the third embodiments have thus been explained. The present disclosure may be carried out in other various modes besides the first to the third embodiments described above.

Figure 13:
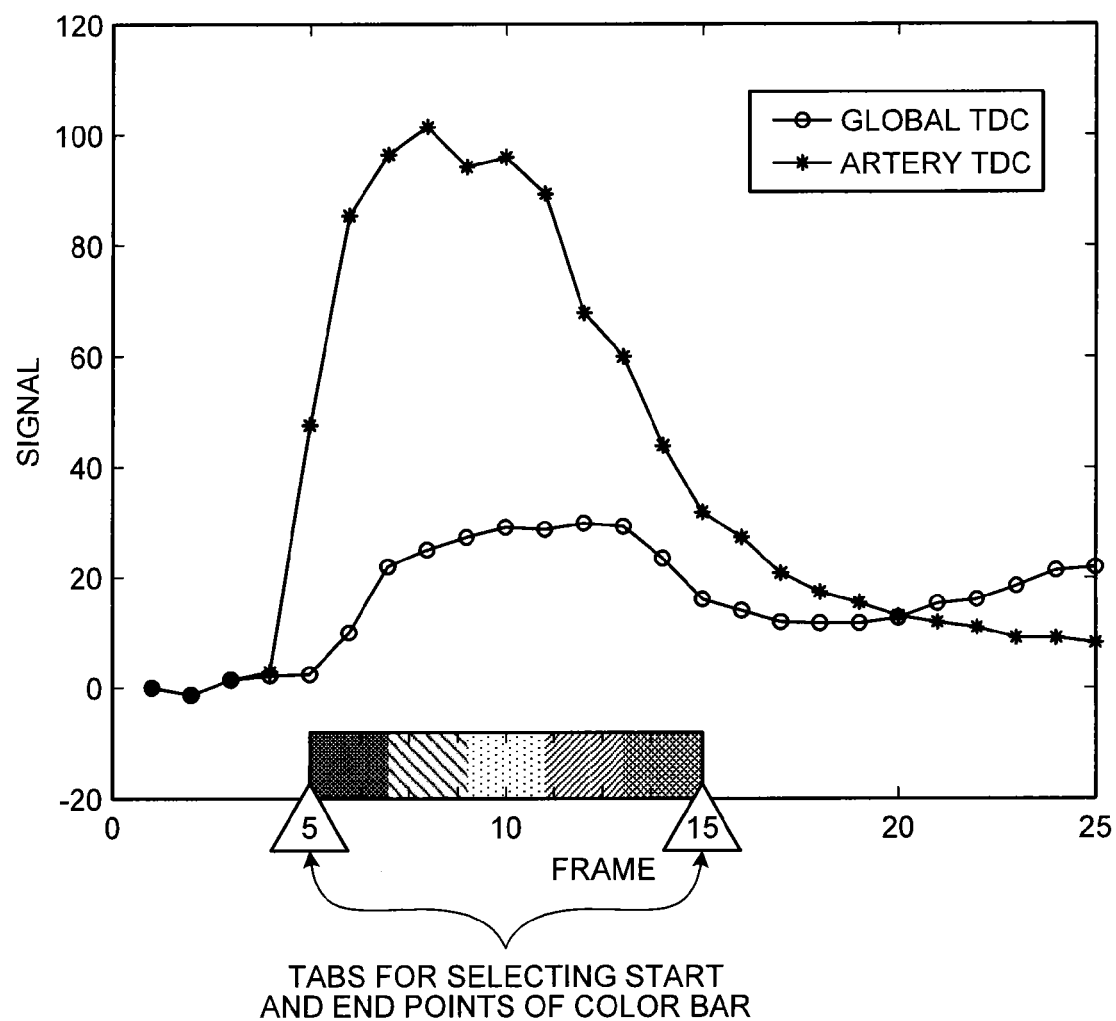
FIG. 13 is a drawing of an example of a Graphical User Interface (GUI) according to a fourth embodiment.

In the first to the third embodiments described above, the examples are explained in which the color bar set by the information converting unit 266 is used; however, possible embodiments are not limited these examples. For instance, the operator may arbitrarily change the start point and the end point of the color bar. FIG. 13 is a drawing of an example of a GUI according to a fourth embodiment. For example, as shown in FIG. 13, the displayed image calculating unit 268 generates a GUI in which the start point and the end point of the color bar can be moved to arbitrary positions and causes the generated GUI to be displayed on the display unit 23, together with an artery TDC and a global TDC. This arrangement makes it possible to fine-tune the range of the colors, and it is therefore possible to provide the images that are easier to view.

In the first to the third embodiments described above, the examples are explained in which the difference images obtained by performing the subtraction process on the mask image and the contrast images are explained. However, possible embodiments are not limited to these examples. It is acceptable if no subtraction process is performed. In that situation, for example, the calculation of the reference values, the normalization of the flow of the contrast material for each of the pixels, and the like are performed by using a plurality of contrast images taken while the contrast material is flowing.

In the third embodiment described above, the example is explained in which the X-ray images, which are monochrome images, and the color images generated by the color image generating unit 267 are superimposed together. However, possible embodiments are not limited to this example. For instance, it is possible to superimpose a plurality of color images (still images) together. In that situation, the displayed image calculating unit 268 causes the plurality of color images generated by the color image generating unit 267 to be displayed in a superimposed manner. In one example, the displayed image calculating unit 268 causes index images before and after a treatment that are expressed in color (e.g., the PT images, the AUC images, the AT images, the MW images, the PH images, the WT images, the "slope" images, and the MTT images) to be displayed on the display unit 23 in a superimposed manner. In this situation, the displayed image calculating unit 268 changes the degree of transparency of one of the superimposed color images, so that the viewer is able to clearly view the upper color image and the lower color image that are superimposed together.

In the first to the third embodiments described above, the example is explained in which the color images, which are still images, are displayed. However, possible embodiments are not limited to this example. For instance, it is acceptable to display a moving picture expressed in color. In that situation, for example, the color image generating unit 267 expresses groups of X-ray images in color by using the color information resulting from the conversion by the information converting unit 266. After that, the displayed image calculating unit 268 causes the display unit 23 to display a moving picture, by arranging the X-ray images expressed in color by the color image generating unit 267 to be displayed successively.

In one example, the color image generating unit 267 extracts frames corresponding to the time period during which a color bar is set, from among the frames contained in the DSA images. After that, the color image generating unit 267 obtains colors corresponding to the time period of the extracted frames from the color bar and assigns the obtained colors to the pixels that have reached the PT. The color image generating unit 267 assigns colors to all the extracted frames. With this arrangement, by displaying these frames successively, it is possible to display a moving picture that renders the manner in which the contrast material is flowing while the colors are changing. When causing the moving picture to be displayed, the displayed image calculating unit 268 adjusts the quantity of frames so that the moving picture ends at the same time as the frame that ends chronologically earlier between the ending frame of the DSA images A and the ending frame of the DSA images B.

In the first to the third embodiments described above, the examples are explained in which the luminosity of the colors such as red and blue is changed. However, possible embodiments are not limited to these examples. For instance, it is acceptable to use a gray scale expressing white to black with levels from bright to dark.

In the first to the third embodiments described above, the processes such as the normalization of the indices using the reference values and the generation of the fitting image are explained. The X-ray diagnosis apparatus 100 according to the fourth embodiment is able to make adjustments so that these processes are performed in stages depending on situations. For example, when a contrast material is injected by using the injector 30 shown in FIG. 1, if the timing for injecting the contrast material is set in advance with respect to the timing for starting an image taking process, the X-ray diagnosis apparatus 100 may exercise control so that index images are generated on the basis of the TDC value in each of the pixels and so that color images are displayed, without normalizing the indices by using the reference values. After that, for example, when the operator performs an operation to transition into the normalizing mode or the fitting image generating mode, the X-ray diagnosis apparatus 100 exercises control so that the processes in the selected mode are performed. With this arrangement, it is possible to speed up the time required by a diagnosis process or an analyzing process. The situation described above is merely an example. The operator is able to arbitrarily arrange a setting according to various situations.

Figure 14:
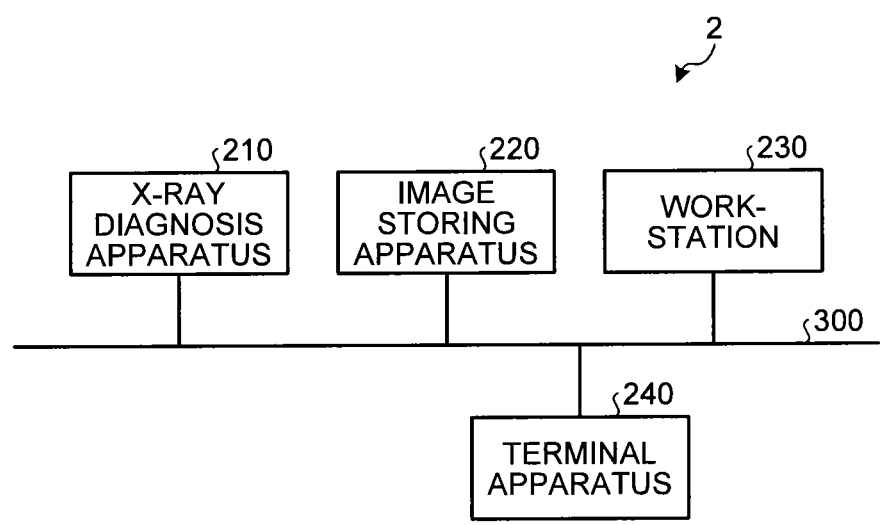
FIG. 14 is a diagram of an exemplary overall configuration of an image processing system including a workstation according to the fourth embodiment.

In the exemplary embodiments described above, the examples are explained in which the X-ray diagnosis apparatus express the angiography images in color. However, the processes described above may be executed by an image processing apparatus such as a workstation. FIG. 14 is a diagram of an exemplary overall configuration of an image processing system including a workstation 230 according to the fourth embodiment.

As shown in FIG. 14, an image processing system 2 according to the fourth embodiment includes an X-ray diagnosis apparatus 210, an image storing apparatus 220, the workstation 230, and a terminal apparatus 240. The apparatuses illustrated in FIG. 14 are, for example, arranged to be able to communicate with one another, either directly or indirectly, via an intra-hospital Local Area Network (LAN) 300 installed in a hospital. For example, if a Picture Archiving and Communication System (PACS) has been introduced into the image processing system 2, the apparatuses transmit and receive medical images and the like to and from one another, according to the Digital Imaging and Communications in Medicine (DICOM) specifications.

The X-ray diagnosis apparatus 210 according to the fourth embodiment takes angiography images related to an intra-vascular treatment. More specifically, the X-ray diagnosis apparatus 210 according to the fourth embodiment takes angiography images before and after a treatment and stores the taken angiography images into a storage area therein. Further, the X-ray diagnosis apparatus 210 transmits the taken angiography images to the image storing apparatus 220.

The image storing apparatus 220 is a database configured to store therein medical images. More specifically, the image storing apparatus 220 according to the fourth embodiment is configured to put the angiography images before and after the treatment that were transmitted from the X-ray diagnosis apparatus 210 into a storage unit and store the angiography images therein. In the fourth embodiment, it is also possible to integrate together the workstation 230 and the image storing apparatus 220 illustrated in FIG. 14, by using the workstation 230 that is able to store images in a large volume. In other words, the fourth embodiment may be configured so that the angiography images before and after the treatment are stored into the workstation 230 itself.

The workstation 230 is an image processing apparatus configured to perform the processes to express the angiography images before and after the treatment in color. More specifically, the workstation 230 according to the fourth embodiment includes the image processing unit 26 illustrated in FIG. 2 and is configured to perform the processes to express, in color, the angiography images before and after the treatment that were taken by the X-ray diagnosis apparatus 210.

The terminal apparatus 240 is an apparatus used for having medical images browsed by a medical doctor or an examination technician who works in the hospital. For example, the terminal apparatus 240 may be configured with a Personal Computer (PC), a tablet-type Personal Computer (PC), a Personal Digital Assistant (PDA), a portable phone, or the like that is operated by a medical doctor or an examination technician who works in the hospital. Further, the terminal apparatus 240 is configured to obtain the color images generated by the workstation 230 via the intra-hospital LAN 300 and causes the obtained color images to be displayed on a monitor. As a result, the viewer who is a medical doctor or an examination technician is able to browse the color images in which the flow of the contrast material is expressed in color.

In the exemplary embodiments described above, the examples in which the X-ray diagnosis apparatus 100 or the workstation 230 executes the processes are explained. However, possible embodiments are not limited to these examples. For instance, the processes may be executed by a service providing apparatus disposed in a network. For example, the service providing apparatus may be disposed at a service center and connected to a terminal apparatus provided in a medical institution via the network. The terminal apparatus provided in the medical institution has a client function to utilize services provided by the service providing apparatus.

As a service, the service providing apparatus provides the terminal apparatus with the same processes as those performed by the X-ray diagnosis apparatus 100. In other words, the service providing apparatus includes functional units that are equivalent to the reference value calculating unit 262, the index image generating unit 263, and the displayed image calculating unit 268. Further, the functional unit equivalent to the reference value calculating unit 262 calculates the reference values used for normalizing the flow of the contrast material on the basis of a chronological transition of the signal intensity of the contrast material in a predetermined region, for each of the plurality of groups of X-ray images chronological taken by using the contrast material. Further, the functional unit equivalent to the index image generating unit 263 normalizes, for each of the plurality of groups of X-ray images, the flow of the contrast material at each of the pixels by using the reference values calculated by the functional unit equivalent to the reference value calculating unit 262 and further generates images in which the features value of the normalized flow of the contrast material are reflected in each of the pixels. Further, the functional unit equivalent to the displayed image calculating unit 268 provides the terminal apparatus with the images generated by the index image generating unit 263. In this situation, the network may be wired or wireless and may be configured with an arbitrary type of communication network such as the Internet or a Wide Area Network (WAN).

The configurations of the X-ray diagnosis apparatus 100 in the first to the third embodiments described above are merely examples. It is possible to integrate or separate any of the functional units as necessary. For example, it is possible to integrate the fitting image generating unit 264 with the inserted image generating unit 265. It is also possible to separate the index image generating unit 263 into a normalization processing unit configured to perform the normalization process by using the reference values and a generating unit configured to generate the index images.

As explained above, according to an aspect of the first to the fourth embodiments, the image processing apparatus and the X-ray diagnosis apparatus disclosed herein make it possible to improve the visibility of the angiography images.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus comprising:
a reference value calculating unit that calculates a reference value used for normalizing a flow of a contrast material, on a basis of a chronological transition of a signal intensity of the contrast material in a predetermined region, for each of a plurality of groups of X-ray images chronologically taken while using the contrast material;
a generating unit that, for each of the plurality of groups of X-ray images, normalizes the flow of the contrast material at each of pixels by using the reference value calculated by the reference value calculating unit and generates an image in which a feature value of the normalized flow of the contrast material is reflected in each of the pixels; and
a display controlling unit that causes a predetermined display unit to display the image generated by the generating unit,
wherein each of the plurality of groups of X-ray images is either a group of images showing a state where the contrast material has been injected or a group of images obtained by subtracting an image taken immediately prior to the injection of the contrast material from each of the images showing the state where the contrast material has been injected.

2. The image processing apparatus according to claim 1, further comprising:
a converting unit that, for each of the feature values, converts information about the feature value at each of the pixels in each of the plurality of groups of X-ray images, into an upper limit value and a lower limit value of color information used for expressing the group of X-ray images in color; and
a color image generating unit that expresses the image generated by the image generating unit in color, by using the color information resulting from the conversion by the converting unit.

3. The image processing apparatus according to claim 1, further comprising: a fitting processing unit that generates a fitting curve by performing a fitting process on each of time-density curves that each indicate the chronological transition of the signal intensity of the contrast material at a corresponding one of the pixels in each of the plurality of groups of X-ray images.

4. The image processing apparatus according to claim 1, wherein the reference value calculating unit calculates at least one of a contrast material injection start time, a contrast material injection time period, a maximum value of an image density, and an accumulated value of image density values, as the reference values.

5. The image processing apparatus according to claim 4, wherein, when the contrast material has been injected to a subject by a contrast material automatic injection device, the reference value calculating unit obtains the contrast material injection start time and the contrast material injection time period from the contrast material automatic injection device.

6. The image processing apparatus according to claim 1, wherein, when a plurality of groups of X-ray images of which contrasts are enhanced at mutually-different times are to be compared with one another, the reference value calculating unit calculates the contrast material injection start times in such a manner that the contrast material injection start times are substantially same among the plurality of groups of X-ray images.

7. The image processing apparatus according to claim 2, wherein the image generating unit normalizes the feature value of the signal intensity of the contrast material by applying the reference value to a time-density curve that indicates the chronological transition of the signal intensity of the contrast material at each of the pixels in each of the plurality of groups of X-ray images, and
the converting unit sets, for each of the feature values of the signal intensity, the upper limit value and the lower limit value of the color information used for expressing the groups of X-ray images in color, by using the feature value of the signal intensity normalized by the generating unit.

8. The image processing apparatus according to claim 1, wherein, to bring a signal intensity maximum time period, which is a time period it takes for the signal intensity to reach a maximum thereof and serves as the feature value of the signal intensity, into correspondence with each of the pixels, the generating unit extracts a first-appearing peak from the plurality of groups of X-ray images by searching in a chronologically forward direction and in a chronologically backward direction and brings one of the two extracted first-appearing peaks into correspondence with the pixel as the signal intensity maximum time period.

9. The image processing apparatus according to claim 2, wherein when a signal intensity maximum time period, which is a time period it takes for the signal intensity to reach a maximum thereof, is used as the feature value of the signal intensity, the converting unit generates frequency distribution data of the signal intensity maximum time period for each of the pixels, extracts a peak corresponding to either a venous phase or an intermediate phase on a basis of the generated frequency distribution data, and sets a time at which the extracted venous phase or the extracted intermediate phase appears as the upper limit value.

10. The image processing apparatus according to claim 1, wherein
when a signal intensity maximum time period, which is a time period it takes for the signal intensity to each a maximum thereof, is used as the feature value of the signal intensity, the generating unit extracts peaks corresponding to an arterial phase, an intermediate phase, and a venous phase, on a basis of a frequency distribution of the signal intensity maximum time periods of the pixels and further classifies a plurality of X-ray images chronologically taken, into the arterial phase, the intermediate phase, and the venous phase on a basis of the extracted peaks, and
the display controlling unit displays each of the X-ray images classified by the generating unit.

11. The image processing apparatus according to claim 2, wherein, on a basis of a signal intensity maximum time period, which is a time period it takes for the signal intensity to reach a maximum thereof, the color image generating unit extracts an arterial phase, an intermediate phase, and a venous phase from the X-ray images and further expresses the extracted arterial, intermediate, and venous phases in color so as to be in mutually-different colors.

12. The image processing apparatus according to claim 2, wherein, from among a plurality of feature values, the color image generating unit selects two feature values as feature values of the signal intensity and further generates a color image in which one of the two selected feature values expresses colors, whereas the other feature value expresses an indicator used for changing a state of the colors, the plurality of feature values including: a signal intensity maximum time period which is a time period it takes for the signal intensity to reach a maximum thereof; an area size of a time-density curve indicating the chronological transition of the signal intensity of the contrast material; a contrast material arrival time which is a time period it takes for the pixel to start being visualized by the contrast material; a half-value width of a peak on the time-density curve; a maximum signal intensity value of the pixel; a contrast material wash-out time period which is a time period from when the pixel exhibits a maximum signal intensity to when the contrast material has finished flowing out; a slope up to the maximum signal intensity; and a mean transit time of the contrast material.

13. The image processing apparatus according to claim 2, wherein the display controlling unit causes either the color image generated by the color image generating unit and one or more of the X-ray images or two or more of the color images generated by the color image generating unit to be displayed in a superimposed manner.

14. The image processing apparatus according to claim 2, wherein
the color image generating unit expresses the groups of X-ray images in color by using the color information resulting from the conversion by the converting unit, and
the display controlling unit causes the predetermined display unit to display a moving picture, by arranging the X-ray images expressed in color by the color image generating unit to be displayed successively.

15. The image processing apparatus according to claim 2, wherein, when a plurality of X-ray images showing blood vessels with enhanced contrast are to be compared with one another, the display controlling unit causes the plurality of X-ray images and color images each of which is generated from a different one of the plurality of X-ray images to be displayed side by side.

16. The image processing apparatus according to claim 2, wherein the display controlling unit causes the predetermined display unit to display, an operating unit making it possible to arbitrarily change the upper limit value and the lower limit value set by the converting unit, a time-density curve indicating the chronological transition of the signal intensity of the contrast material in the predetermined region of each of the plurality of groups of X-ray images.

17. The image processing apparatus according to claim 3, further comprising: an inserted image generating unit configured to generate an inserted image which is an image to realize an arbitrary frame rate, by using the fitting curve generated by the fitting processing unit.

18. The image processing apparatus according to claim 1, further comprising: a pre-processing unit that performs a pre-processing process including a position misalignment correction and a noise removal related to a movement of a subject, on each of the plurality of groups of X-ray images chronologically taken while using the contrast material.

19. An X-ray diagnosis apparatus comprising:
a reference value calculating unit that calculates a reference value used for normalizing a flow of a contrast material, on a basis of a chronological transition of a signal intensity of the contrast material in a predetermined region, for each of a plurality of groups of X-ray images chronologically taken while using the contrast material;
a generating unit that, for each of the plurality of groups of X-ray images, normalizes the flow of the contrast material at each of pixels by using the reference value calculated by the reference value calculating unit and generates an image in which a feature value of the normalized flow of the contrast material is reflected in each of the pixels; and
a display controlling unit that causes a predetermined display unit to display the image generated by the generating unit,
wherein each of the plurality of groups of X-ray images is either a group of images showing a state where the contrast material has been injected or a group of images obtained by subtracting an image taken immediately prior to the injection of the contrast material from each of the images showing the state where the contrast material has been injected.

* * * * *